(12) United States Patent
Caruthers et al.

(10) Patent No.: US 11,230,565 B2
(45) Date of Patent: Jan. 25, 2022

(54) SYNTHESIS OF BACKBONE MODIFIED MORPHOLINO OLIGONUCLEOTIDES AND CHIMERAS USING PHOSPHORAMIDITE CHEMISTRY

(71) Applicant: THE REGENTS OF THE UNIVERSITY OF COLORADO, Denver, CO (US)

(72) Inventors: Marvin Caruthers, Boulder, CO (US); Sibasish Paul, Boulder, CO (US)

(73) Assignee: THE REGENTS OF THE UNIVERSITY OF COLORADO, Denver, CO (US)

(*) Notice: Subject to any disclaimer, the term of this patent is extended or adjusted under 35 U.S.C. 154(b) by 0 days.

(21) Appl. No.: 16/359,776

(22) Filed: Mar. 20, 2019

(65) Prior Publication Data

US 2019/0218236 A1 Jul. 18, 2019

Related U.S. Application Data

(63) Continuation-in-part of application No. PCT/US2017/051839, filed on Sep. 15, 2017.

(60) Provisional application No. 62/397,277, filed on Sep. 20, 2016, provisional application No. 62/513,089, filed on May 31, 2017.

(51) Int. Cl.
*C07F 9/6558* (2006.01)
*C07F 9/44* (2006.01)
*C07F 9/6561* (2006.01)

(52) U.S. Cl.
CPC ........ *C07F 9/65583* (2013.01); *C07F 9/4461* (2013.01); *C07F 9/6561* (2013.01); *Y02P 20/55* (2015.11)

(58) Field of Classification Search
CPC ... C07F 9/65583; C07F 9/6561; C07F 9/4461
See application file for complete search history.

(56) References Cited

U.S. PATENT DOCUMENTS

| | | | | |
|---|---|---|---|---|
| 7,205,399 B1* | 4/2007 | Vargeese | ................ | C07H 21/00 536/22.1 |
| 7,943,762 B2* | 5/2011 | Weller | ................ | C12N 15/1132 536/31 |
| 2009/0002408 A1 | 1/2009 | Azami et al. | | |
| 2009/0088562 A1 | 4/2009 | Weller et al. | | |
| 2009/0131632 A1* | 5/2009 | Fox | ................ | C08G 65/33317 528/399 |
| 2012/0296087 A1* | 11/2012 | Sinha | ................ | C07F 9/65586 544/69 |
| 2015/0038462 A1 | 2/2015 | Iversen et al. | | |
| 2016/0040162 A1 | 2/2016 | Bestwick et al. | | |
| 2016/0076033 A1 | 3/2016 | Torii et al. | | |
| 2019/0218236 A1 | 7/2019 | Caruthers et al. | | |

FOREIGN PATENT DOCUMENTS

EP 2623507 A1 8/2013
WO 2017024264 A2 2/2017

OTHER PUBLICATIONS

Sibasish et al. "Oxidative Substitution of Boranephosphonate Diesters as a Route to Post-synthetically Modified DNA" JACS 137, pp. 3253-3264. (Year: 2015).*
Zhang et al. (Tetrahedron Letters (2008), 49(22), 3570-3573 (Year: 2008).*
European Search Report dated Apr. 14, 2020 in EP Application No. 17 85 3706, 8 pages.
Abramova TV et al: "Synthesis of morpholine nucleoside triphosphates". Tetrahedron Letters, Elsevier Ltd, Amsterdam, NL, vol. 45, No. 22, May 24, 2004 (May 24, 2004), pp. 4361-4364, XP004506361, ISSN: 0040-4039, DOI: 10.1016/J.TETLET.2004.03.193, 4 pages.
Bhadra Jhuma et al: "Synthesis of phosphorodiamidate morpholino oligonucleotides by H-phosphonate method", Tetrahedron Letters, vol. 56, No. 31, 2015, pp. 4565-4568, XP029213857. ISSN: 0040-4039, DOI: 10.1016/J.TETLET.2015.05.080, 4 pages.
International Search Report dated Dec. 4, 2017 in International Application No. PCT/US2017/051839.
Written Opinion dated Dec. 4, 2017 in International Application No. PCT/US2017/051839.
Examination Report No. 1 from Australian Patent Office in Application No. 2017330276 dated Jan. 22, 2021.
Zhang, N., et al, "Synthesis and properties of morpholino chimeric oligomuleotides", Tetrahedron Letters, (2008) vol. 49, No. 22, pp. 3570-3573.
Sibasish et al. "Oxidative Substitution of Boranephosphonate Diesters as a Route to Postsynthetically Modified DNA", J. Am. Chem. Soc. 2015. vol. 137, pp. 3253-3264, entire document, especially:p. 3253, col. 1, para 2; p. 3253, col. 2, para 1; p. 3254, Figure 1A; p. 3255, Table 1, Entry 3; p. 3256, Scheme 1.
Taro Harakawa et al. "Development of an efficient method for phosphorodiamidate bond formation b using inorganic salts", Bioorganic & Medicinal Chemistry Letters22 (2012) 1445-1147.

* cited by examiner

*Primary Examiner* — Jezia Riley
(74) *Attorney, Agent, or Firm* — Berg Hill Greenleaf & Ruscitti LLP

(57) ABSTRACT

Amine substituted morpholino oligonucleotides, other than the classical N,N-dimethylamino PMO analogue, and methods of efficiently synthesizing these oligonucleotides with high yield are provided. Morpholino oligonucleotides having thiophosphoramidate, phosphoramidate, and alkyl phosphoramidate linkers. Chimeras containing unmodified DNA/RNA and other analogs of DNA/RNA can be prepared. These oligonucleotides form duplexes with complementary DNA or RNA that are more stable than natural DNA or DNA/RNA complexes, are active with RNAse H1, and may be transfected into cells using standard lipid reagents. These analogues are therefore useful for numerous applications.

15 Claims, 11 Drawing Sheets

SYNTHESIS OF BACKBONE MODIFIED MORPHOLINO OLIGONUCLEOTIDES AND CHIMERAS USING PHOSPHORAMIDITE CHEMISTRY

CROSS REFERENCE TO RELATED APPLICATIONS

This application is a continuation-in-part of PCT Application No. PCT/US17/51839, having an international filing date of Sep. 15, 2017, which designated the United States, which PCT application claims the benefit of U.S. Provisional Patent Application Ser. No. 62/513,089, filed 31 May 2017, and U.S. Provisional Patent Application Ser. No. 62/397,277, filed 20 Sep. 2016. Each of these priority documents are incorporated herein by reference in their entirety.

TECHNICAL FIELD

This disclosure relates to methods of synthesizing morpholino oligonucleotides and derivatives thereof.

BACKGROUND

Morpholino oligonucleotides show promise for use as antisense oligonucleotide therapeutics due to their high affinity for DNA and RNA, resistance to various nucleases, stability in vivo, and low toxicity. Phosphorodiamidate morpholino oligonucleotides (PMOs; compound 3, FIG. 1A) have nonionic inter-nucleotide linkages and a morpholino replacing the deoxyribose of DNA. These N,N-dimethylaminophosphoradiamidate morpholino oligonucleotides inhibit gene expression by preventing translation while interfering with RNA-splicing (Summerton, J. Biochim. Biophys. Acta 1999, 1489, 141-158), are resistant to cellular nucleases (Hudziak, et al. Antisense Nucleic Acid Drug Dev. 1996, 6, 267-272; Arora, et al. J. Pharm. Sci. 2002, 91, 1009-18.), and have higher RNA binding affinity than DNA (Summerton, J. E. Morpholinos and Related Antisense Biomolecules (Janson, C. G., and During, M. J., Eds.), 2003, Kluwer/Plenum Publishers.). Therapeutic development of PMOs is underway, for example in clinical trials for the treatment of Duchenne Muscular Dystrophy (DMD), and preventing infection of the hemorrhagic filovirus Marburg (US Patent Publications 2016/0040162 and 2015/0038462). Additionally, PMOs have been investigated for applications in nanotechnology (Paul, et al., Chem. Commun., 2013, 49, 11278-80) and surface hybridization (Tercero, et al., J. Am. Chem. Soc., 2009, 131:4953).

Unfortunately, these promising applications for PMOs are severely limited by the lack of an efficient synthesis methodology. In contrast to standard methods for chemically preparing DNA and RNA on an automated synthesizer, PMOs are currently synthesized in a 5' to 3' direction on a polystyrene resin. As a first step, condensation of the 5'-hydroxyl-N-trityl-morpholino nucleoside with N,N-dimethylaminodichlorophosphoramidate generates the N,N-dimethylaminochlorophosphoroamidate synthon. Coupling in the presence of a base yields the dimer attached to the resin. Further detritylation with acid generates a dimer that can be elongated by repeating the cycle. There are several recognized problems with this approach. For example, condensation yields are low (recovered yield for dithymidine morpholino was 45%) and require long reaction times. Moreover, the 5'-chloro-phosphoroamidate monomers are unstable, and coupling two morpholino monomers in the presence of large amount of base is difficult (Bhadra, et al., Tetrahedron Letters 2015, 56: 4565-68). Additionally, this approach requires special procedures, techniques, and materials (e.g. swellable polystyrene resins, unique reaction vessels, and the pyridinium salt of trifluoroacetic acid as the detritylating agent) that are not readily available in most laboratories.

Recently, a new method has been developed using H-phosphonate chemistry for the synthesis of polythymidine PMOs. There are also problems with this approach. For example, because the phosphorus atom in H-phosphonates is electrophilic and lacks a lone pair of electrons, it is much more resistant to oxidation under ambient conditions than most P(III) compounds. Moreover, the coupling yields for the formation of H-phosphonate morpholino dimers are low (77%).

Each of the foregoing disadvantages are overcome by the methods of this disclosure. Additionally, the methods of this disclosure achieve other advantages discussed more fully below.

SUMMARY

This disclosure provides new methods for synthesizing phosphorodiamidate morpholinos (PMOs) and PMO-DNA chimeras. These methods are very robust as oligomers containing phosphosphorodiamidate internucleotide linkages can be prepared using phosphoramidite chemistry, in high yield on automated DNA synthesizers. The process begins by incorporating morpholino phosphoramidites into DNA, boronation, and then oxidation with iodine in the presence of various amines in order to form a diverse set of PMOs and PMO-DNA chimeras. The method is general and leads to the synthesis of a large number of PMO linkages. Unlike procedures that use chlorophosphoramidate synthons, the more reactive phosphordiamidite synthons of this disclosure may be used to synthesize these analogues in high yields. Selective activation, via dicyanoimidazole, of the diisopropylamino component of the morpholino phosphordiamidite during coupling is used to assemble these analogs.

Advantageously, the PMO and PMO-DNA chimeras may be synthesized on a DNA synthesizer because both the morpholino phosphordiamidate and 2'-deoxynucleoside synthons were designed for synthesis of oligonucleotides in a 3' to 5' direction, which is not the case with previously developed chemistries in which the N,N-dimethylamino PMO synthons are designed for synthesizing these analogues in a 5' to 3' direction. Moreover, this new approach builds upon using a boranephosphoramidate internucleotide linkage that can be used to generate a large variety of PMO chimeras through iodine oxidation with an appropriate amine. For example, PMO-LNA, PMO-RNA, PMO-DNA phosphorothioate/phosphorodithioate, and PMO-DNA phosphonoacetate/phosphonoformate chimeras, among others, can be prepared using these methods.

Relative to their potential use in various biological and biochemical applications, these PMO-DNA chimeras exhibited three possible advantages over several other analogues. For example, aminomorpholino phosphorodiamidate derivatives were found to form a more stable duplex with complementary DNA or RNA than either unmodified DNA/RNA or the standard N,N-dimethylamino PMO analogue (approx. 1.75 times more stable per modification with RNA than the N,N-dimethyl analogue). Additionally, these PMO-DNA chimeras are active with RNAse H1. This is encouraging relative to the standard N,N-dimethylamino PMO analogs in which the completely substituted PMO is inactive with RNase H1. These cap/gap N,N-dimethylamino PMO chimeras activate RNase H1 thereby providing an analog with different biochemical properties (for example the aminoamidate derivative has enhanced stability toward duplex formation) that is useful for various applications in biology. Due to the increased stabilization of these PMO-DNA chimeras with complementary RNA (relative to the unmodified duplexes), this kind of cap/gap analogue decreases off-target effects because shorter, single-stranded antisense oligonucleotides can be used. Moreover, these PMO-DNA chimeras can easily be transfected into cells using common, well known transfecting reagents, which eliminates problems associated with delivery of PMOs by such procedures as microinjection, hybridization of PMOs with DNA and delivery with ethoxylated polyethylenimine, or conjugation with either peptides, or dendritic molecular transporters.

Thus, this disclosure provides PMO synthesis methodologies that provide efficient and cost-efficient methods of synthesizing PMO derivatives with the formation of few side products. These synthesis methods incorporate the inventors' previously reported stereoselective conversion of boranephosphonate DNA, in the presence of iodine and amines, to phosphoramidate DNA (Paul, S., Roy, S., Monfregola, L., Shang, S., Shoemaker, R., Caruthers, M. H., J. Am. Chem. Soc. 2015, 137:3253-64), resulting in three significant advantages of the synthesis methods of this disclosure:

1) These methods are orthogonal and compatible with standard DNA/RNA synthesis methods using phosphoramidite chemistry, and therefore PMO synthesis can be carried out on a regular DNA synthesizer;
2) For the first time, PMOs having internucleotide linkages other than N,N-dimethylaminophosphoroamidate-morpholino can be synthesized; and,
3) These synthesis methods allow for the synthesis of PMO-DNA chimeras. Because these chimeras are anionic, they are water soluble, hybridize to RNA, and thus activate RNase H.

This Summary is neither intended nor should it be construed as being representative of the full extent and scope of the present invention. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

BRIEF DESCRIPTION OF FIGURES

FIG. 7A and FIG. 7D are images of fluorescein localization of ODN 27. FIG. 7B and FIG. 7E are images of DAPI localization of nuclei in the same cells. FIG. 7C is an image overlay of images from FIG. 7A and FIG. 7B. FIG. 7F is a phase contrast image of the cells shown in FIG. 7D.

DESCRIPTION OF EMBODIMENTS

Figure 1A:
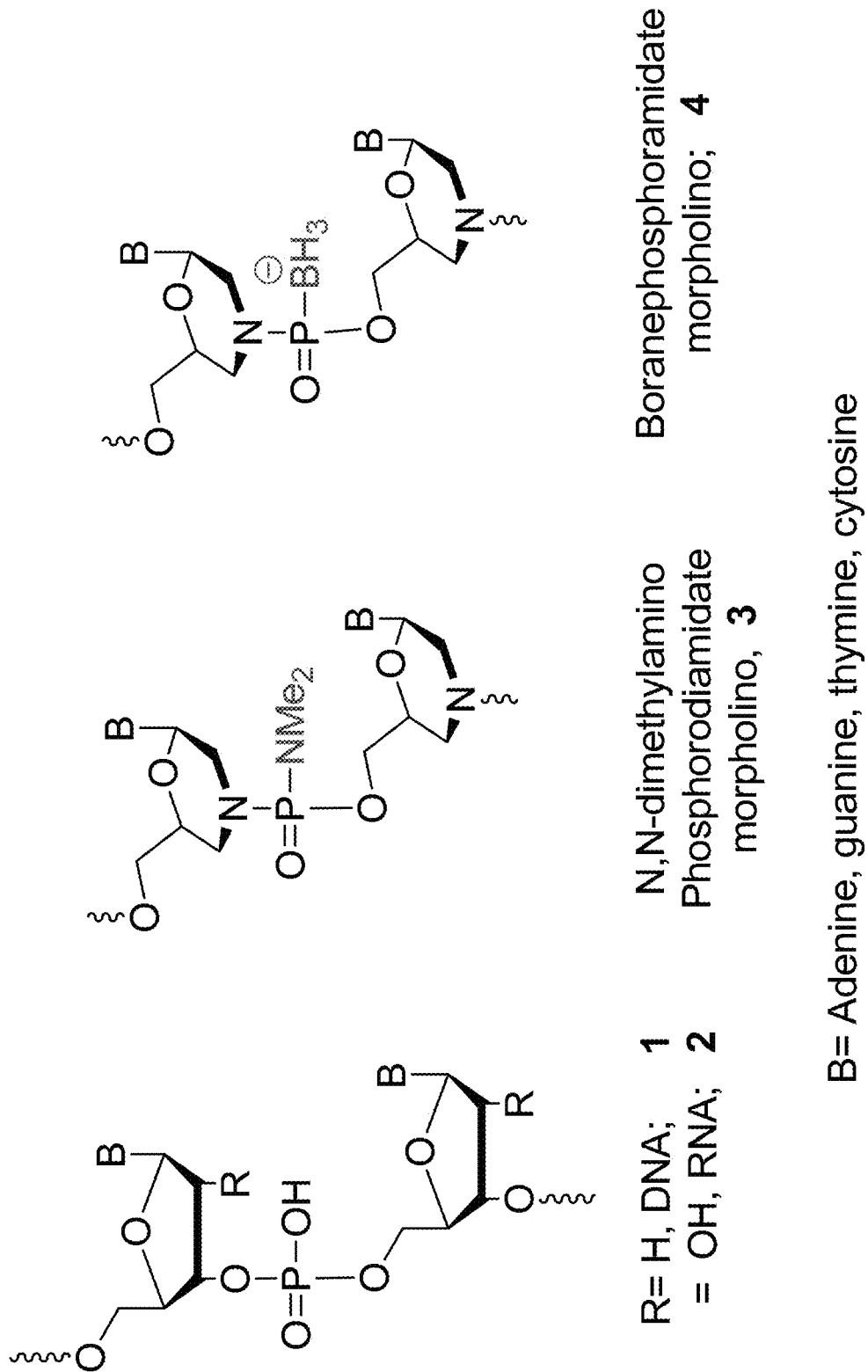
FIG. 1A shows the chemical structures of DNA (1), RNA (2), N,N-dimethylamino phosphordiamidate morpholino (3), and borane phosphoramidate morpholino (4) oligonucleotides.

The terms below have the following meanings, unless indicated otherwise:

The term "oligonucleotide analog" refers to oligonucleotide having a modified backbone structure, e.g., a backbone other than the standard phosphodiester linkage found in natural oligo- and polynucleotides, and optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A "nucleic acid base" is not particularly limited as long as it can be used for the synthesis of nucleic acid and includes, for example, a pyrimidine base such as cytosine group, uracil group, thymine group and the like, and a purine base such as adenine group, guanine group and the like. The "optionally protected nucleic acid base" means, for example, that an amino group may be protected in an adenine group, a guanine group, or a cytosine group, which is a nucleic acid base having an amino group, and a nucleic acid base wherein the amino group therein is protected by a protecting group sustainable under the deprotection conditions of the morpholine ring nitrogen atom of the morpholino nucleotide is preferable.

The "amino-protecting group" is not particularly limited, and examples thereof include the protecting groups described in Greene's PROTECTIVE GROUPS IN ORGANIC SYNTHESIS, 4th edition, Wiley-Interscience, 2006 and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methyl sulfonyl)ethanol, 2-(phenyl sulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like.

In some cases, the carbonyl-protecting group does not need to be particularly introduced. Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, monoalkylamino, dialkylamino, carboxy, cyano, nitro etc.) at any position(s), are also encompassed in the "nucleic acid base."

A substantially uncharged, phosphorus containing backbone in an oligonucleotide analog is one in which a majority of the subunit linkages, e.g., between 60-100%, are uncharged at physiological pH, and contain a single phosphorous atom. The analog contains between 5 and 40 subunits, typically about 8-25 subunits, and preferably about 12 to 25 monomeric subunits. The analog may have exact sequence complementarity to the target sequence or near complementarity, as defined below.

A "monomer" or "subunit" of an oligonucleotide analog refers to one nucleotide (or nucleotide analog) unit of the analog. The term may refer to the nucleotide unit with or without the attached inter-subunit linkage, although, when referring to a "charged subunit", the charge typically resides within the inter-subunit linkage (e.g. a phosphate or phosphorothioate linkage).

A "morpholino oligonucleotide analog" is an oligonucleotide analog composed of morpholino subunit structures. Exemplary structures are shown side-by-side (for comparative purposes) in FIG. 1B (structures 4-7), where the structures are linked together by phosphorus-containing linkages, one to three atoms long, joining the morpholino nitrogen of one subunit to the 5' exocyclic carbon of an adjacent subunit, and "B" moieties are purine or pyrimidine base-pairing moieties effective to bind, by base-specific hydrogen bonding, to a base in a polynucleotide. The purine or pyrimidine base-pairing moiety is typically adenine, cytosine, guanine, uracil, or thymine. The synthesis, structures, and binding characteristics of morpholino oligomers are described in detail in U.S. Pat. Nos. 5,698,685; 5,217,866; 5,142,047; 5,034,506; 5,166,315; 5,521,063; and 5,506,337, all of which are incorporated herein by reference.

Figure 1B:
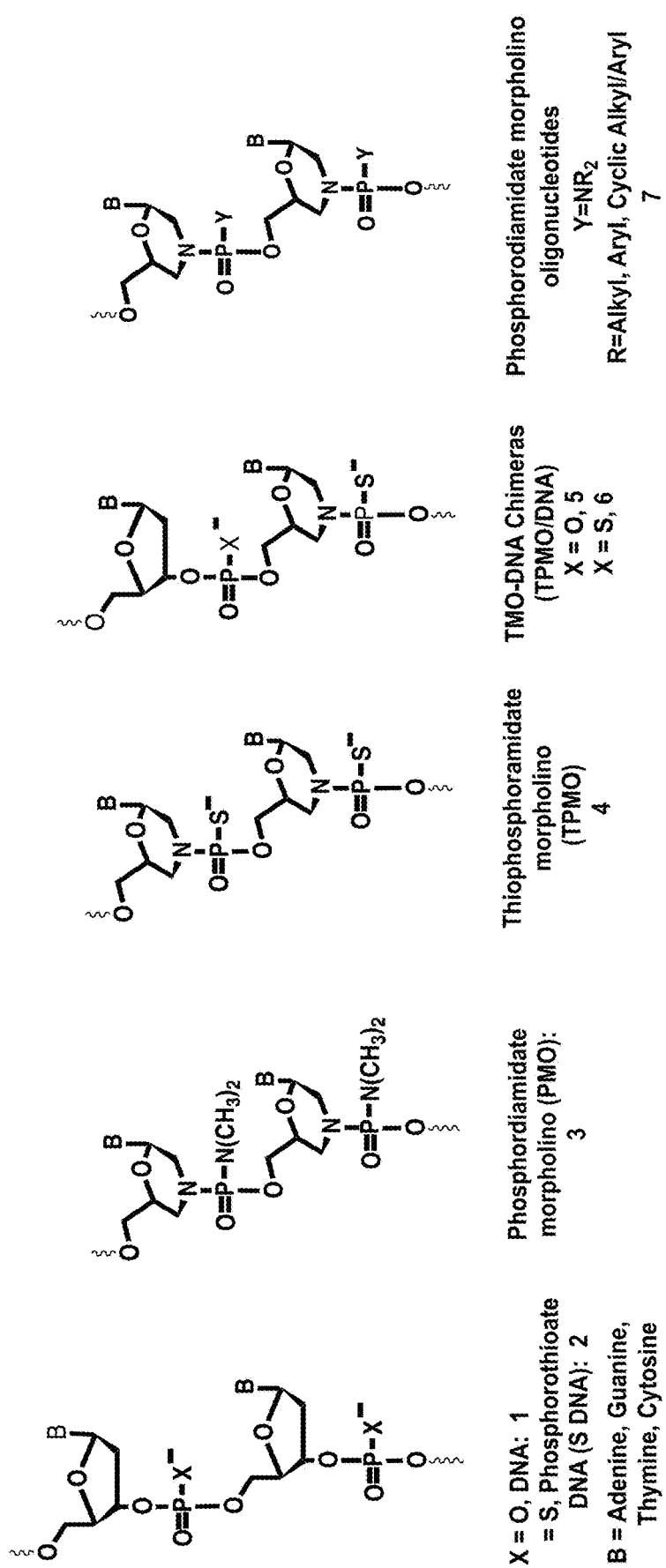
FIG. 1B shows the chemical structures of (1) DNA, (2) RNA, (3) N,N-Dimethylamino phosphordiamidate morpholino (PMO), (4) Thiomorpholino Oligonucleotide (TMO), (5,6) Thiomorpholino 2'-Deoxynucleotide Chimeras (TMO/DNA) and (7) Phosphorodiamidate morpholino oligonucleotides.
Figure 2:
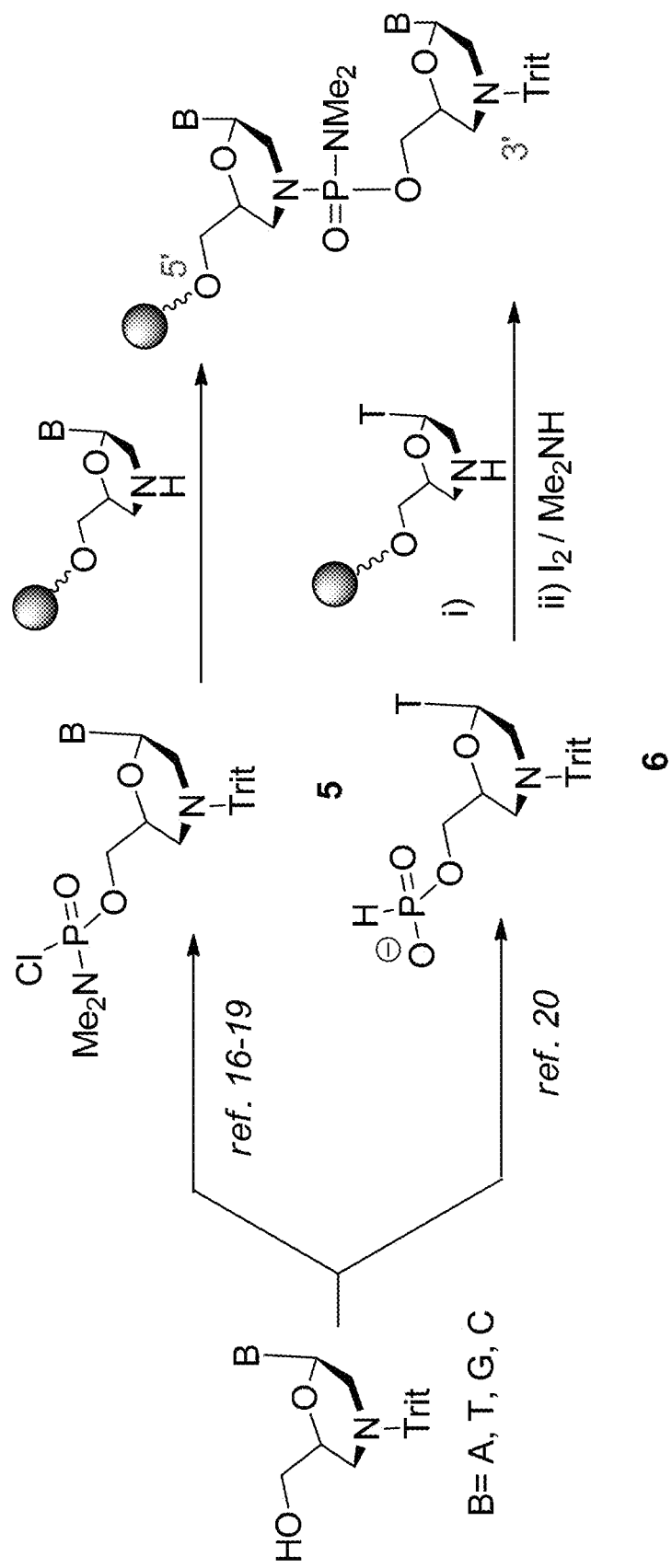
FIG. 2 is a synthesis scheme depicting current approaches for the synthesis of N,N-dimethylamino phosphorodiamidate morpholino oligonucleotides. Note that in numbering of the morpholino, the primary hydroxyl group should be 6', but for the purposes of this disclosure, this hydroxyl group is marked as 5' in order to correlate with regular nucleic acid chemistry.

The subunits and linkages shown in FIG. 1B (structures 4-7) are used for six-atom repeating-unit backbones, (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom linking the 5' exocyclic morpholino carbon to the phosphorus group may be sulfur, nitrogen, carbon, or oxygen. The X moiety pendant from the phosphorus is any stable group which does not interfere with base-specific hydrogen bonding, including fluoro, alkyl, alkoxy, thioalkoxy, and alkyl amino, including cyclic amines, all of which can be variously substituted, so long as base-specific bonding is not disrupted. Alkyl, alkoxy, and thioalkoxy may include 1-10 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Y is sulfur or oxygen.

A preferred morpholino oligomer is either a phosphorodiamidate-linked morpholino oligomer, referred to herein as a PMO or a morpholino oligomer referred to herein as a TMO or TMO/DNA chimera. Such oligomers are composed of morpholino subunit structures such as shown in FIG. 1B (structures 4-7), where Y=NH$_2$, NHR, or NR$_2$ (where R is lower alkyl, preferably methyl), X=O or S, and B are purine or pyrimidine base-pairing moieties effective to bind, by base-specific hydrogen bonding, to a base in a polynucleotide. Also preferred are structures with an alternate phosphorodiamidate linkage, where, in FIG. 1B, Y=lower alkoxy, such as methoxy or ethoxy, Y=NH or NR, where R is lower alkyl.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

Sequences are described as "complementary" to one another when hybridization occurs in an antiparallel configuration. A double-stranded polynucleotide can be "complementary" to another polynucleotide. A targeting sequence may have "near" or "substantial" complementarity to the target sequence and still function for the purpose of the present invention. Preferably, the oligonucleotide analogs of this disclosure have at most one mismatch with the target sequence out of 10 nucleotides, and preferably at most one mismatch out of 20. Alternatively, the antisense oligomers of this disclosure have at least 90% sequence homology, and preferably at least 95% sequence homology, with the exemplary targeting sequences as designated herein. Thus, the oligomers made by the methods of this disclosure are particularly useful as therapeutic antisense molecules when administered to treat a disease state amenable to antisense therapy.

An oligonucleotide analog "specifically hybridizes" to a target polynucleotide if the oligomer hybridizes to the target under physiological conditions, with a Tm substantially greater than 45° C., preferably at least 50° C., and typically 60° C.-80° C., or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

The oligonucleotide analogs of this disclosure preferably specifically bind to a target RNA sequence inside a cell. The base specificity of such binding is sequence specific. For example, a single-stranded polynucleotide can specifically bind to a single-stranded polynucleotide that is complementary in sequence.

As detailed above, the antisense oligomer has a base sequence directed to a targeted portion of the viral genome, preferably either the 5'-CS or 3'-CS. In addition, the oligomer is able to effectively target infecting viruses, when administered to an infected host cell, e.g. in an infected animal subject. This requirement is met when the oligomer compound (a) has the ability to be actively taken up by mammalian cells, and (b) once taken up, form a duplex with the target ssRNA with a Tm greater than about 50° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the oligomer to the cell cytoplasm.

The following methods are useful for testing any given, substantially uncharged backbone for its ability to meet these requirements:

Active or Facilitated Uptake by Cells

The antisense oligomer may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its inter-subunit linkages are uncharged at physiological pH. Experiments carried out in support of this technology indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates. The net charge is preferably neutral or at most 1-2 net charges per oligomer.

In addition to being substantially or fully uncharged, the antisense agent is preferably a substrate for a membrane transporter system (i.e., a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin™, containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked to the 5' or 3' end of the antisense oligomer. The peptide is typically 8-16 amino acids and consists of a mixture of arginine, and other amino acids including phenyalanine and cysteine. Exposure of cells to the peptide conjugated oligomer results in enhanced intracellular uptake and delivery to the RNA target.

Alternatively, the requisite properties of oligomers with any given backbone can be confirmed by a simple in vivo test, in which a labeled compound is administered to an animal, and a body fluid sample, taken from the animal several hours after the oligomer is administered, is assayed for the presence of heteroduplex with target RNA.

Substantial Resistance to RNaseH

Two general mechanisms have been proposed to account for inhibition of expression by antisense oligonucleotides. In the first, a heteroduplex formed between the oligonucleotide and the viral RNA acts as a substrate for RNaseH, leading to cleavage of the target RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing, translation, or replication. This class includes methylphosphonates, morpholino oligonucleotides, peptide nucleic acids (PNA's), certain 2'-O-allyl or 2'-O-alkyl modified oligonucleotides, and N3'→P5' phosphoramidates.

A test oligomer can be assayed for its RNaseH resistance by forming an RNA:oligomer duplex with the test compound, then incubating the duplex with RNaseH under standard assay conditions. After exposure to RNaseH, the presence or absence of intact duplex can be monitored by gel electrophoresis or mass spectrometry.

In Vivo Uptake

Rapid tests exist for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the target RNA when administered to a mammalian subject, and the heteroduplex subsequently appears in the urine (or other body fluid). Details of this method are given in U.S. patent application Ser. No. 09/736,920, entitled "Non-Invasive Method for Detecting Target RNA" (Non-Invasive Method), the disclosure of which is incorporated herein by reference. Briefly, a test oligomer containing a backbone to be evaluated, having a base sequence targeted against a known RNA, is injected into an animal, e.g., mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

Exemplary Oligomer Backbones

Figure 4A:
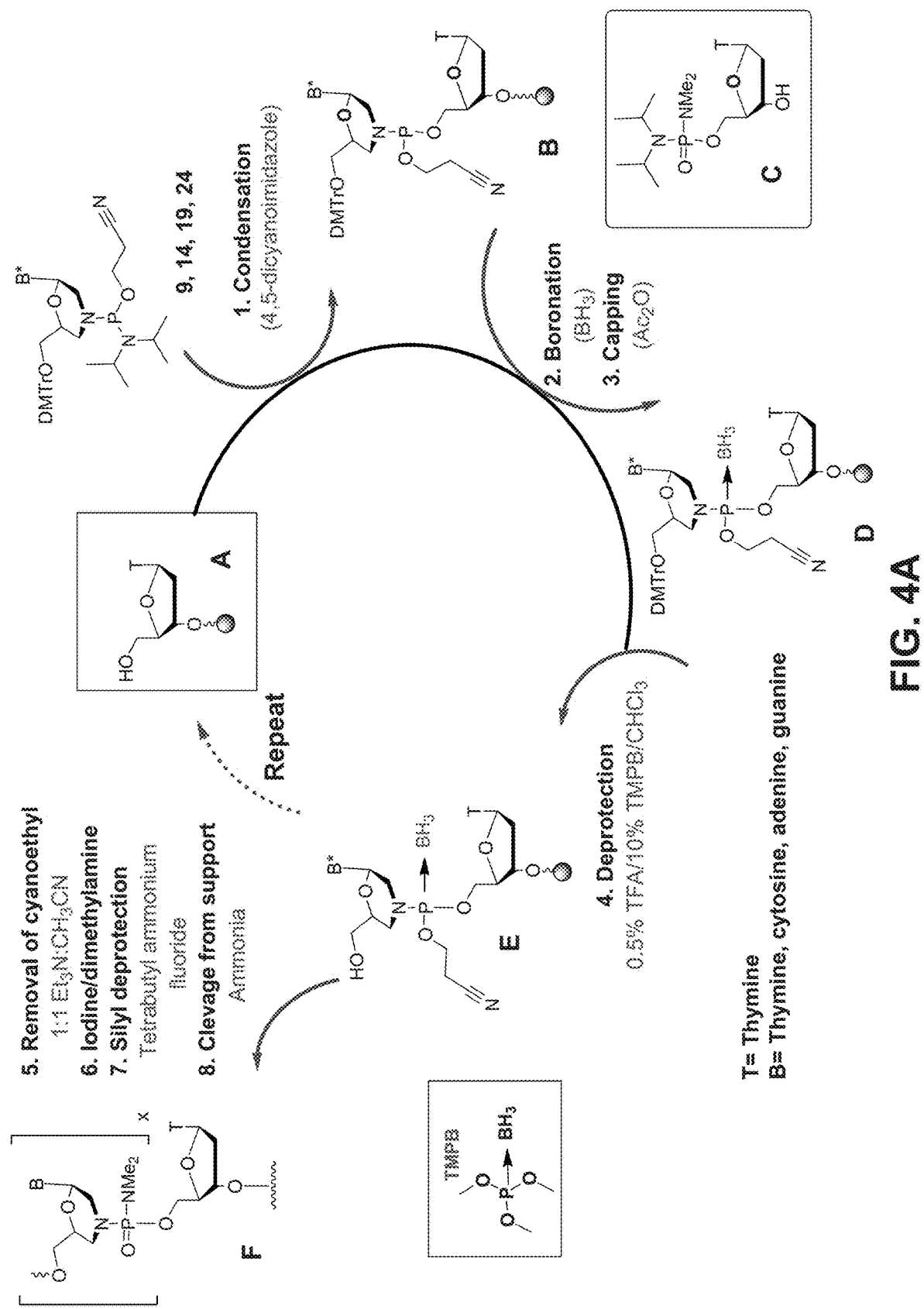
FIG. 4A shows the synthesis scheme for solid phase synthesis for phosphordiamidate morpholino oligonucleotides (PMOs) using BIBS-protected phosphoramidites. Compound F is a PMO having only N,N-dimethylamino-phosphorodiamidate internucleotide linkages; "x" is a selected number of N,N-dimethylamino-PMO nucleotide units; Compound A is a thymidine deoxyribonucleoside, but this deoxyribonucleoside can be replaced by any of the four 2'-deoxyribonucleosides or morpholino nucleosides. In instances in which the cytosine, adenine, and guanine bases are used, they must be protected with the bis(tertbutyl)isopropylsilyl (BIBS) group.

Examples of nonionic linkages that may be used in oligonucleotide analogs are shown in FIG. 4. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (R=O) and carbamate (R=NH$_2$) linkages; alkyl phosphonate and phosphotriester linkages (R=alkyl or —O— alkyl); amide linkages; sulfone and sulfonamide linkages ($R_1$, $R_2$=CH$_2$); and a thioformacetyl linkage (2E). The latter is reported to have enhanced duplex and triplex stability with respect to phosphorothioate antisense compounds. Also reported are the 3'-methylene-N-methylhydroxyamino compounds.

A preferred oligomer structure employs morpholino-based subunits bearing base-pairing moieties, joined by uncharged linkages. Morpholino oligonucleotides, including antisense oligomers, are detailed, for example, in co-owned U.S. Pat. Nos. 5,698,685; 5,217,866; 5,142,047; 5,034,506; 5,166,315; 5,185,444; 5,521,063; and 5,506,337, all of which are expressly incorporated by reference herein.

Important properties of the morpholino-based subunits include: the ability to be linked in an oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNAse degradation.

Backbone structures for antisense oligonucleotides of this disclosure include the morpholino subunit types shown in FIG. 4, linked by an uncharged, phosphorus-containing subunit linkage. FIG. 4 shows a phosphorus-containing linkage which forms the five atom repeating-unit backbone, where the morpholino rings are linked by a 1-atom phosphoamide linkages. FIG. 4 shows a linkage which produces a 6-atom repeating-unit backbone. In this structure, the atom linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Y moieties are sulfur or oxygen, and are preferably oxygen.

As noted above, the substantially uncharged oligomer may advantageously include a limited number of charged linkages, e.g. up to about 1 per every 5 uncharged linkages, more preferably up to about 1 per every 10 uncharged linkages. Therefore, a number of charged linkages, e.g. charged phosphoramidate or phosphorothioate, may also be incorporated into the oligomers.

Another aspect of this disclosure provides methods of producing morpholino-containing oligonucleotide analogs, comprising starting with a 5'-unprotected-2'-deoxyribonucleoside linked to a polystyrene support, and reacting this 5'-unprotected-2'-deoxyribonucleoside with a phosphoramidite synthon (i.e., monomer) in anhydrous acetonitrile containing 4,5-dicyanoimidazole (DCI) to generate a dimer having a phosphoramidite diester internucleotide linkage. The dimer is then chemically activated by either boronating, sulfurizing, or oxidizing the dimer. The dimer is then capped and detritylated. These steps (adding a phosphoramidite synthon through the steps of capping and detritylating) are repeated as desired to elongate the oligomer by adding monomers to the growing oligomer (growing step-wise from a dimer, to a trimer, to a tetramer, pentamer, hexamer, etc.). The morpholino phosphoroamidate oligomers are then contacted with iodine and dimethylamine in tetrahydrofuran to convert morpholino boranephosphoroamidate to N,N-dimethylamino PMOs. The oligomers are then contacted with a solution comprising ammonium hydroxide and ethylene diamine to remove the oligomer from the polystyrene support. These repetitive monomer additions to the oligomer may be performed on a common commercial DNA synthesizer, thereby greatly enhancing the efficiency and speed of the synthesis in a cost-effective manner.

Exemplary monomers for use in the synthesis methods of this disclosure include phosphordiamidites having a chemical structure selected from the group consisting of:

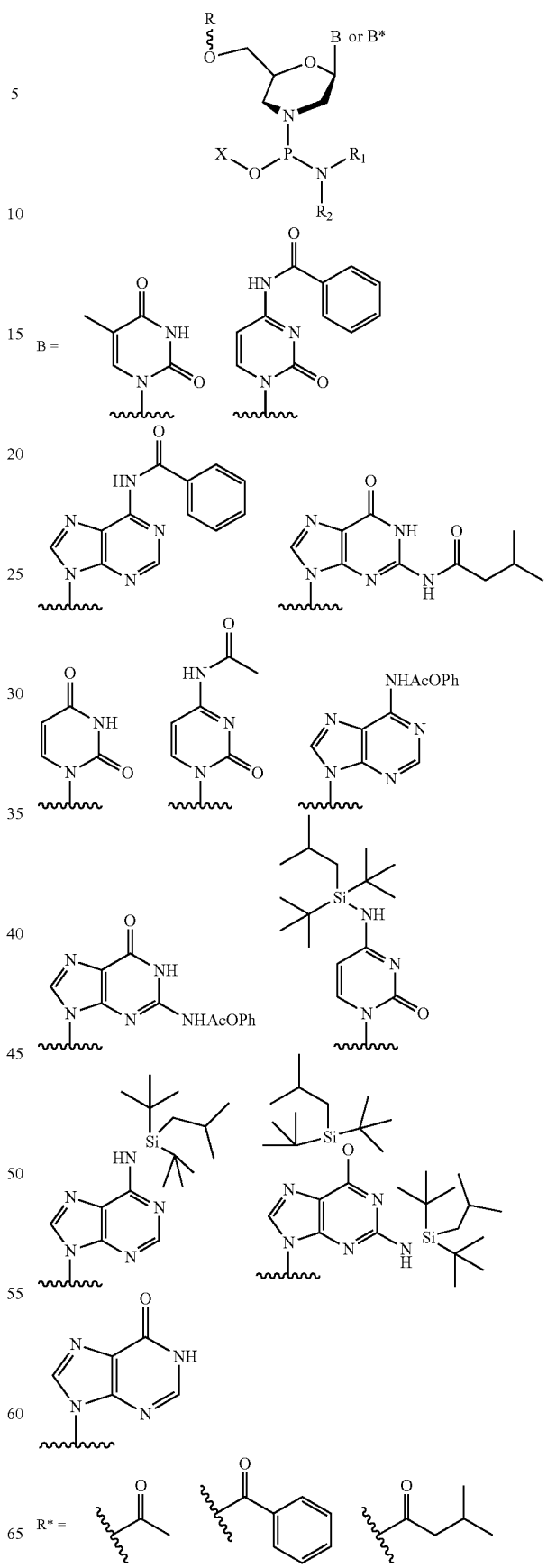

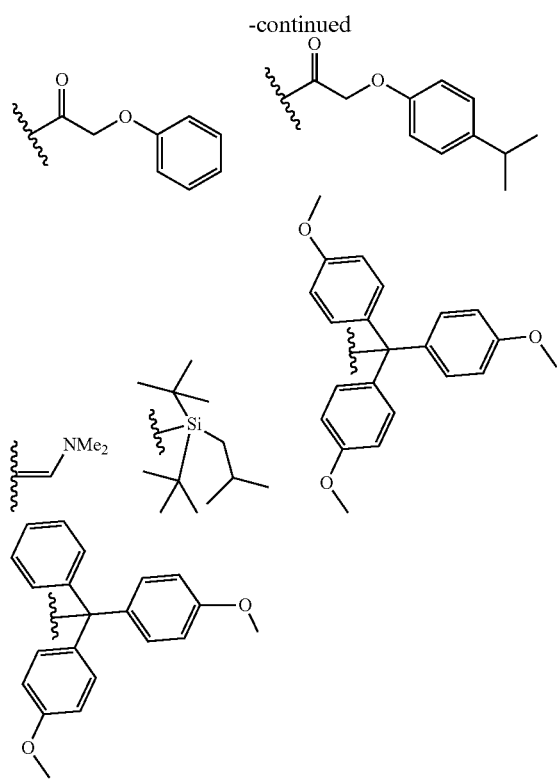

Wherein:

B or B* may be a silyl protecting group, or acid labile or base labile protecting group;

X=Cyanoethyl or its derivative, alkyl, thio alkyl, thio carbonyl, carboxylate, acetate, or formate derivatives R=Dimethoxytrityl, trimethoxyltrityl, or any silyl based protecting group $R_1$ and $R_2$ are independently isopropyl, $C_{2-20}$ linear or branched alkyl chain, or a 5-7 membered aliphatic ring.

Each publication or patent cited herein is incorporated herein by reference in its entirety.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1

Figure 3A:
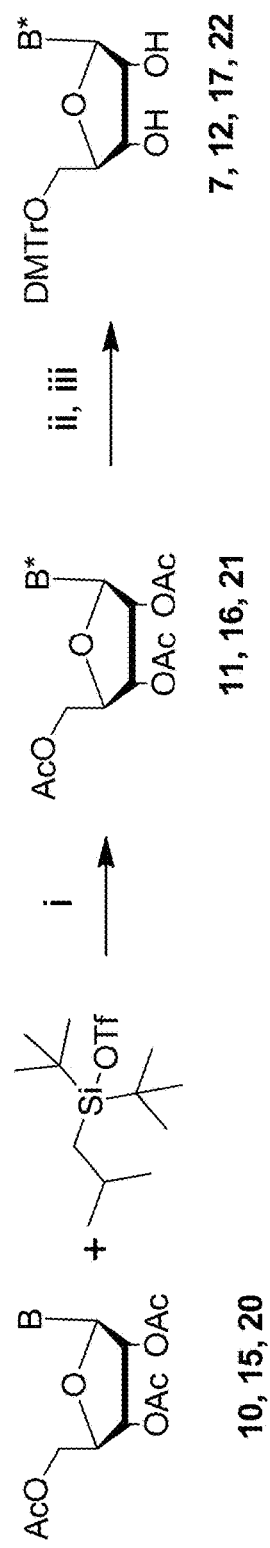
FIG. 3A is a synthesis scheme depicting synthesis of BIBS protected-morpholino phosphordimidite synthons. Reaction conditions: (i) Lutidine (4.0 equiv) and 1,4-dioxane; (ii) 1.0 M $NH_3$/MeOH; (iii) DMT-Cl (1.2 equiv), pyridine; and (iv) $NaIO_4$ (1.1 equiv), $(NH_4)_2B_4O_7$ (1.1 equiv), MeOH; (v) $NaCNBH_3$ (2.0 equiv), AcOH (2.0 equiv), MeOH; (vi) $P(OCH_2CH_2CN)(NiPr_2)_2$ (1.2 equiv), 4,5-dicyanoimidazole (0.5 equiv), and $CH_2Cl_2$.
Figure 3A:
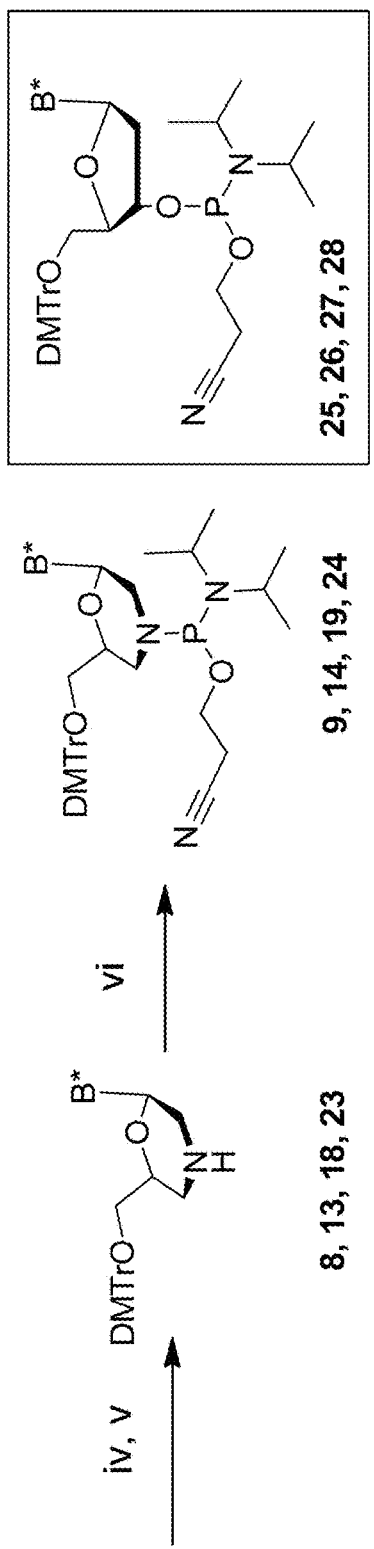
Figure 3A:
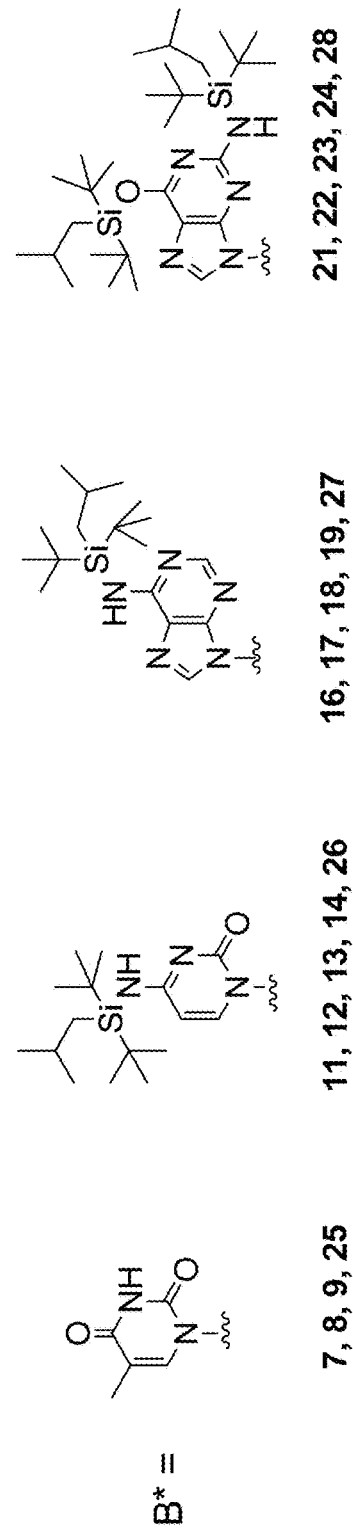
Figure 3B:
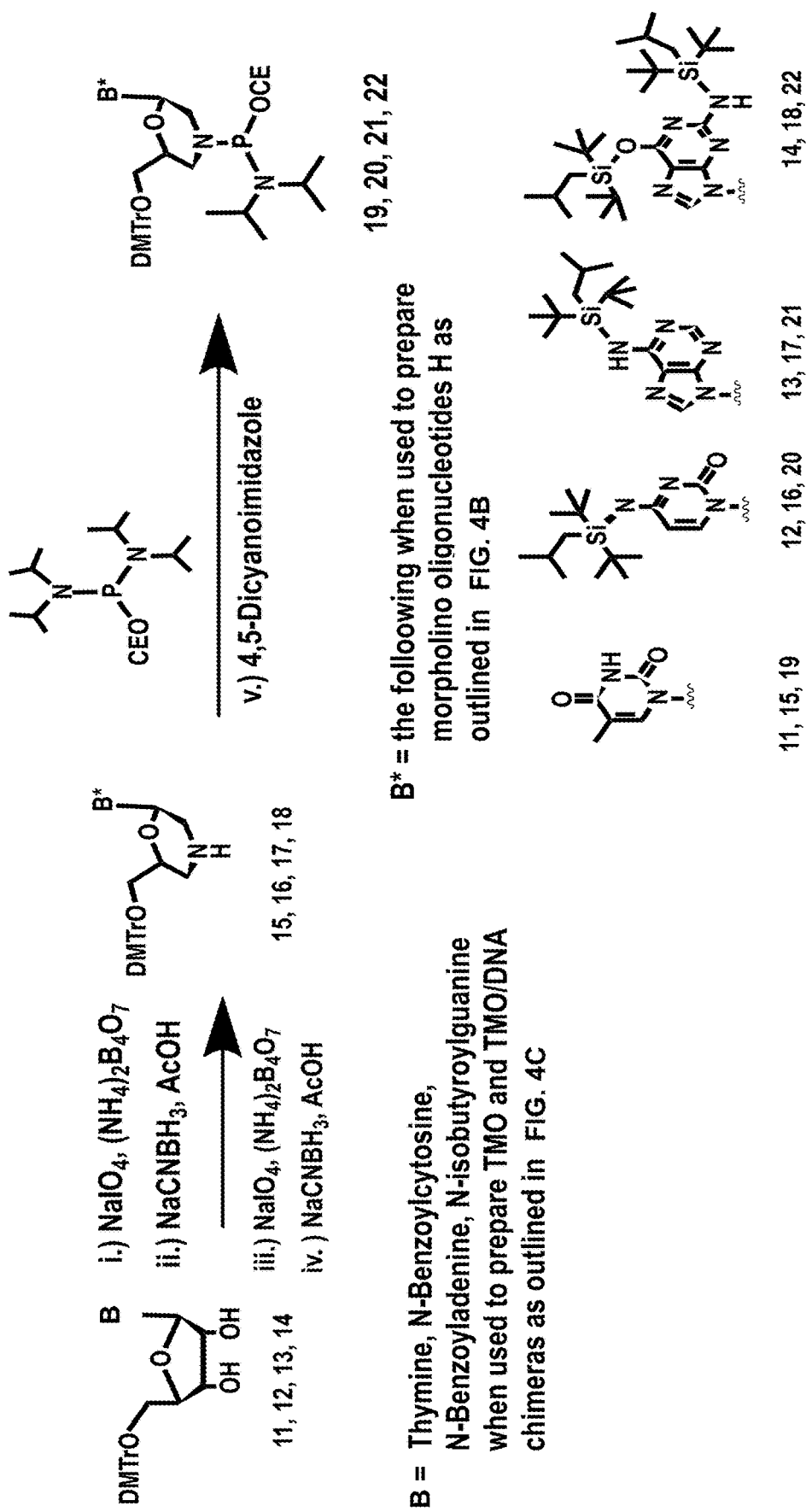
FIG. 3B is another synthesis scheme depicting preparation of morpholino phosphordiamidite synthons (19, 20, 21, 22). Reaction conditions: (i) Lutidine (4.0 equiv) and 1,4-dioxane; (ii) 1.0 M $NH_3/CH_3OH$; (iii) $NaIO_4$ (1.1 equiv), $(NH_4)_2B_4O_7$ (1.1 equiv), $CH_3OH$; (iv) $NaCNBH_3$ (2.0 equiv), AcOH (2.0 equiv), $CH_3OH$; (v) $P(OCH_2CH_2CN)(NiPr_2)_2$ (1.2 equiv), 4,5-dicyanoimidazole (0.5 equiv) in $CH_3CN$.

Synthesis of N-Di-Tertbutylisobutyl Protected Morpholino Phosphoradimidites Phosphoradiamidite synthons were developed for all four bases that are needed to generate the boranephosphoramidate morpholino linkages (see the synthesis scheme of FIGS. 3A and 3B). Synthesis of the phosphoradiamidite thymidine morpholino monomer synthon was carried out following literature protocols (Zhang, et al., Tetrahedron Letters 2008, 49, 3570; Pattanayak, et al., Nucleosides, Nucleotides and Nucleic Acids, 2012, 31, 763-782). Ribothymidine was first treated with dimethoxytrityl chloride (DMT-Cl) in anhydrous pyridine under argon atmosphere to produce 5'O-DMTr-ribothymidine (compound 11, FIG. 3B), which was treated with sodium periodate, followed by ammonium biborate to produce 2',3'-dihydroxyl-morpholino-thymidine (not shown). Reduction of 2' and 3' hydroxyl groups was carried out (without further purification) using sodium cyanoborohydride under mild acidic conditions to produce the thymine morpholino monomer (compound 15, FIG. 3B). The building block thymidine synthon (compound 19, FIG. 3B) was then prepared by phosphitylation of compound (compound 15, FIG. 3B) with 2-cyanoethyl-N,N,N',N'-tetraisopropyl phosphorodiamidite and 4,5-dicyanoimidazole (DCI) in dichloromethane under argon atmosphere with 86% yield. The thymidine synthon (compound 19, FIG. 3B) does not require base protection.

The inventors also synthesized 5'-dimethoxytrityl-morpholinothymidine-3'-O-methyl-N,N-diisopropylphosphoradiamidite following a similar protocol, but the solid phase coupling with the cyanoethyl phosphoradiamidite was found to be more efficient than the O-methyl counterpart.

Synthesis of the corresponding monomers of cytosine, adenine, and guanine was initiated by first protecting the nucleoside amino groups with bis(tert-butyl)isobutylsilyl (BIBS) using a variation of the protocol reported previously (Roy, S., Olesiak, M., Shang, S., Caruthers, M. H., J. Am. Chem. Soc. 2013, 135:6234-41).

The reaction of 5',3',2'-tri-O-acetylcytidine (10) with BIBS-OTf (Tf=triflate) in the presence of 2,6-lutidine gave 76% yield of the BIBS-protected cytidine after 2 h stirring at 60° C. under an argon atmosphere. But the synthesis of the corresponding adenine and guanosine required much longer reaction times (3 days) with yields of 25-31% for BIBS-protected guanosine and 74% for the corresponding adenosine derivative. As depicted in the synthesis scheme of FIG. 3B, these protected (silylated) ribonucleosides were first treated with ammonium hydroxide to remove the acetyl protecting groups, converted to the 5'-dimethoxy-trityl compounds (compounds 12, 13, 14), and then the morpholino derivatives (16, 17, 18). These compounds were used to generate the phosphordiamidite synthons 20, 21, and 22.

General Procedure for Synthesis of Morpholino Nucleosides.

5'-Dimethoxytrityl protected nucleosides were dissolved in methanol followed by addition of 1.2 equivalents of sodium periodate and ammonium biborate tetrahydrate (1.2 equivalents). Mixtures were stirred at room temperature for three hours when TLC indicated complete consumption of starting material. The reaction mixtures were filtered through a pad of celite and added to activated, powdered 4 A° molecular sieves (0.4 g/mmol) followed by addition of 2.0 equivalents each of sodium cyanoborohydride and glacial acetic acid. Reaction mixtures were then stirred for 4-5 h when the intermediate diol was completely reduced. Reaction mixtures were filtered through a pad of celite and evaporated to dryness. Products were dissolved in chloroform and washed with saturated $NaHCO_3$ and brine. Organic layers were collected, dried over $Na_2SO_4$ and filtered, and solvent removed under reduced pressure. Products were purified by flash chromatography on a silica gel column. In all cases, the silica gel slurries were prepared with the starting eluant mixture containing an additional 5% triethylamine. After pouring the slurry, columns were washed with two column volumes of the starting solvent mixture containing no triethylamine. Compounds 15, 16, and 17 in FIG. 3B were eluted using a gradient of chloroform to 19:1 chloroform:methanol. Compound 18 was purified using a gradient of 1:1 ethylacetate:hexanes to 7:3 ethylacetate:hexanes. All the yields described in the following sections represent those obtained over two steps starting from the 5'-dimethoxytrityl-N-BIBS protected nucleosides.

5'-Dimethoxytritylmorpholinothymidine (compound 15, FIG. 3B): Yield: 53%. $^1$H NMR (CDCl$_3$, 400 MHz) δ: 7.46-7.44 (2H, m), 7.35-7.20 (7H, m), 6.85-6.81 (4H, m), 5.78-5.75 (1H, dd), 4.02-3.98 (1H, m), 3.79 (6H, s), 3.28-3.25 (1H, m), 3.16-3.12 (1H, dd), 3.08-3.04 (2H, m), 2.43 (3H, s). $^{13}$C NMR (CDCl$_3$) δ: 164.22, 158.49, 150.45, 144.72, 135.90, 135.78, 135.32, 130.06, 130.03, 128.12, 127.81, 126.83, 113.10, 113.09, 110.82, 86.02, 80.90, 64.43, 55.20, 45.93, 11.84. ESI-MS (m/z): 561.2314 (M+H)$^+$.

N$^4$-Di(tert-butyl)isobutylsilyl-5'-dimethoxytritylmorphohnocytidine (compound 16, FIG. 3B): Yield: 64%. $^1$H NMR (CDCl$_3$, 400 MHz) δ: 7.59-7.58 (1H, d), 7.53-7.51 (2H, m), 7.41-7.25 (7H, m), 6.91-6.87 (4H, m), 5.88-5.87 (1H, d), 5.79-5.76 (1H, dd), 4.70 (1H, bs), 4.03-4.00 (1H, m), 3.82 (6H, s), 3.29-3.24 (2H, m), 3.14-3.10 (1H, m), 3.04-3.00 (1H, d), 2.67-2.62 (1H, m), 2.52-2.46 (1H, m), 2.15-2.08 (1H, m), 1.18-1.17 (19H, m), 1.07-1.03 (8H, m). $^{13}$C NMR (CDCl$_3$) δ: 168.25, 158.63, 154.57, 145.06, 140.50, 136.02, 135.95, 130.06, 130.02, 128.11, 127.88, 126.73, 113.06, 96.35 88.95, 81.76, 77.94, 64.70, 55.17, 50.01, 47.32, 46.30, 28.68, 26.24, 26.14, 24.82, 21.02, 20.72, 20.67, 11.65. ESI-MS (m/z): 727.4047 (M+H)$^+$.

N$^6$-Di(tert-butyl)isobutylsilyl-5'-dimethoxytritylmorpholinoadenosine (compound 17, FIG. 3B):Yield: 61%. $^1$H NMR (CDCl$_3$, 400 MHz) δ: 8.38 (1H, s), 8.01 (1H, s), 7.51-7.48 (2H, m), 7.39-7.24 (7H, m), 6.88-6.85 (4H, m), 5.90-5.86 (1H, dd), 4.11-4.08 (1H, m), 3.82 (6H, s), 3.33-3.26 (2H, m), 3.15-3.10 (2H, m), 2.79-2.73 (1H, m), 2.19-2.12 (1H, m), 1.22-1.02 (27H, m). $^{13}$C NMR (CDCl$_3$) δ: 158.64, 158.11, 152.55, 148.92, 144.97, 144.96, 137.76, 135.90, 130.04, 128.06, 127.80, 126.74, 121.60, 121.52, 117.79, 117.71, 113.04, 86.06, 80.44, 76.89, 64.39, 60.14, 59.88, 50.16, 49.93, 48.49, 47.36, 47.12, 46.08, 46.00, 43.93, 43.83, 43.71, 26.82, 26.28, 26.19, 24.80, 24.36, 24.27, 24.18, 21.04, 20.81, 20.79, 20.35, 20.07. ESI-MS (m/z): 751.4238 (M+H)$^+$.

N$^2$—O$^6$-Bis[di(tert-butyl)isobutylsilyl-5'-dimethoxytrityltrimorpholino guanosine (compound 18, FIG. 3B): Yield: 47%. $^1$H NMR (CDCl$_3$, 400 MHz) δ: 7.80 (1H, s), 7.51-7.49 (2H, m), 7.39-7.32 (6H, m), 7.28-7.25 (1H, m), 6.89-6.87 (4H, m), 5.74-5.71 (1H, m), 4.05 (1H, bs), 3.82 (6H, s), 3.31-3.26 (1H, m), 3.23-3.15 (2H, m), 3.13-3.07 (1H, m), 2.76-2.70 (1H, m), 2.26-2.19 (1H, m), 2.15-2.09 (1H, m), 1.93 (1H, bs), 1.21-1.18 (36H, m), 1.09-1.07 (2H, m), 1.03-0.99 (16H, m). $^{13}$C NMR (CDCl$_3$) δ: 160.69, 159.39, 158.62, 154.10, 145.01, 135.56, 135.85, 130.02, 128.06, 127.79, 126.73, 116.84, 113.06, 85.99, 80.73, 77.41, 64.42, 60.23, 49.83, 47.78, 26.31, 24.89, 24.72, 21.94, 21.40, 20.73. ESI-MS (m/z): 965.5944 (M+H)$^+$.

Referring again to FIG. 3B, the procedure for the synthesis of appropriately protected synthons (compounds 19, 20, 21, and 22, FIG. 3B) is as follows:

The 5'-O-DMT-N-BIBS protected morpholino nucleosides (compounds 16, 17, and 18, FIG. 3B), described above, and the 5'-O-DMTr protected morpholino thymidine nucleoside (compound 15, FIG. 3B) were dried overnight in vacuum. They were dissolved in anhydrous CH$_2$Cl$_2$ followed by addition of 1.2 equivalents of 2-cyanoethyl-N,N,N',N'-tetraisopropyl phosphorodiamidite under argon. After adding 0.5 equivalent of 4,5-dicyanoimidazole, the reaction was allowed to proceed with stirring for 5 h under an argon atmosphere at room temperature. At this time, TLC indicated complete conversion of the starting materials. Reaction mixtures were diluted with CH$_2$Cl$_2$, washed first with a 5% NaHCO$_3$ solution, and then brine. The organic layers were dried over Na$_2$SO$_4$, filtered, and evaporated to dryness. The products were purified by silica gel column chromatography. The silica gel slurry was prepared with the starting eluant mixture containing an additional 5% triethylamine. After pouring the slurry, the column was washed with two column volumes of the starting solvent mixture containing no triethylamine. Phosphordiamidite compounds (compounds 19, 20, 21, and 22 of FIG. 3B) were purified using a gradient of 3:7 ethylacetate:hexanes to 1:1 ethylacetate:hexanes.

5'-O-Dimethoxytritylmorpholinothymine-3'-O-cyanoethyl-N,N-diisopropyl phosphordiamidite (compound 19, FIG. 3B): Yield: 86%. $^{31}$P NMR (CD$_2$Cl$_2$) δ: 127.21, 126.08. $^1$H NMR (CD$_2$Cl$_2$, 400 MHz) δ: 9.51 (1H, bs), 7.50-7.47 (2H, m), 7.38-7.25 (8H, m), 6.89-6.86 (4H, m), 5.78-5.75 (0.5H, dd), 5.65-5.62 (0.5H, dd), 4.08-4.02 (1H, m), 3.99-3.86 (3H, m), 3.82 (6H, s), 3.65-3.52 (2H, m), 3.48-3.34 (1H, m), 3.31-3.27 (1H, m), 3.13-3.09 (1H, m), 2.75-2.68 (2H, m), 2.53-2.47 (2H, m), 1.96 (3H, m), 1.25-1.18 (12H, m). $^{13}$C NMR (CD$_2$Cl$_2$) δ: 164.02, 163.96, 158.66, 150.13, 144.95, 135.92, 135.90, 135.79, 135.68, 135.52, 129.99, 128.07, 127.77, 126.77, 117.89, 117.74, 113.05, 110.48, 110.39, 86.05, 80.54, 80.49, 80.20, 77.36, 77.21, 64.37, 60.09, 59.84, 55.20, 49.05, 48.83, 47.58, 47.06, 46.83, 45.87, 45.78, 43.91, 43.74, 24.36, 24.29, 24.22, 24.20, 20.77, 20.33, 20.66, 12.29. ESI-MS (m/z): 727.4047 (M+H)$^+$.

N$^4$-Di(tert-butyl)isobutylsilyl-5'-dimethoxytrityl-morpholinocytosine-3'-O-cyanoethyl-N,N-diisopropylphosphordiamidite (compound 20, FIG. 3B): Yield: 83%. $^{31}$P NMR (CD$_2$Cl$_2$) δ: 126.32, 124.88. $^1$H NMR (CD$_2$Cl$_2$, 400 MHz) δ: 7.58-7.55 (1H, m), 7.50-7.48 (2H, m), 7.38-7.31 (6H, m), 7.28-7.24 (1H, m), 6.88-6.85 (4H, m), 5.79-5.76 (1.5H, m), 5.63-5.59 (0.5H, m), 4.54 (1H, bs), 4.04-3.87 (3H, m), 3.82 (6H, s), 3.74-3.71 (0.5H, m), 3.65-3.45 (3H, m), 3.30-3.24 (1.5H, m), 3.14-3.10 (1H, m), 2.80-2.75 (1H, m), 2.71-2.68 (1H, m), 2.55-2.46 (1H, m), 2.38-2.31 (1H, m), 2.11-2.07 (1H, m), 1.78 (1H, bs), 1.25-1.15 (31H, m), 1.04-1.02 (8H, m). $^{13}$C NMR (CD$_2$Cl$_2$) δ:168.14, 158.61, 154.46, 144.98, 140.62, 140.42, 135.98, 135.88, 130.03, 128.07, 127.75, 126.71, 117.96, 117.75, 113.02, 96.20, 96.09, 85.97, 81.68, 81.34, 81.23, 77.05, 77.00, 64.50, 60.21, 60.09, 59.85, 55.18, 49.63, 49.41, 47.98, 47.13, 46.18, 45.91, 45.83, 43.96, 43.84, 43.77, 28.58, 26.21, 26.07, 24.78, 24.38, 24.26, 24.17, 24.12, 20.98, 20.76, 20.71, 20.62, 20.31, 20.23. ESI-MS (m/z): 927.5329 (M+H)$^+$.

N$^6$-Di(tert-butyl)isobutylsilyl-5'-dimethoxytritylmorpholinoadenine-3'-O-cyanoethyl-N,N-diisopropylphosphordiamidite (compound 21, FIG. 3B): Yield: 79%. $^{31}$P NMR (CD$_2$Cl$_2$) δ: 127.96, 125.36. $^1$H NMR (CD$_2$Cl$_2$, 400 MHz): 8.38-8.37 (1H, d), 8.01-8.00 (1H, d), 7.51-7.48 (2H, m), 7.38-7.31 (6H, m), 7.28-7.24 (1H, m), 6.88-6.86 (4H, m), 5.93-5.90 (0.5H, m), 5.82-5.79 (0.5H, m), 5.39 (1H, bs), 4.14-4.10 (0.5H, m), 4.06-4.02 (0.5H, m), 4.0-3.90 (2H, m), 3.82 (6H, s), 3.71-3.63 (1H, m), 3.60-3.52 (2.5H, m), 3.42-3.37 (0.5H, m), 3.34-3.30 (1H, m), 3.17-3.13 (1H, m), 3.02-2.91 (1H, m), 2.78-2.75 (1H, m), 2.72-2.68 (1H, m), 2.66-2.59 (1H, m), 1.26-1.18 (31H, m), 1.10-1.08 (8H, m). $^{13}$C NMR (CD$_2$Cl$_2$) δ: 158.64, 158.11, 152.55, 148.92, 144.97, 137.76, 135.92, 135.80, 130.02, 128.06, 127.77, 126.74, 121.60, 117.79, 117.71, 113.04, 86.50, 80.50, 80.44, 80.34, 80.22, 76.94, 76.81, 64.39, 60.14, 59.91, 55.18, 50.16, 49.93, 48.49, 48.44, 47.35, 47.12, 46.08, 46.00, 43.95, 43.83, 43.71, 28.62, 26.28, 26.19, 24.80, 24.35, 24.29, 24.18, 21.04, 20.79, 20.36, 20.27. ESI-MS (m/z): 951.5437 (M+H)$^+$.

$N^2,O^6$-bis[di(tert-butyl)isobutylsilyl]-5'-dimethoxytrityl-morpholinoguanine-3'-O-cyanoethyl-N,N-diisopropylphosphoradiamidite (compound 22, FIG. 3B): Yield: 82%. $^{31}$P NMR (CD$_2$Cl$_2$) δ: 127.62, 126.99. $^1$H NMR (CD$_2$Cl$_2$, 400 MHz): 7.79-7.76 (1H, d), 7.49-7.45 (2H, m), 7.37-7.29 (6H, m), 7.27-7.23 (1H, m), 6.87-6.84 (4H, m), 5.76-5.64 (1H, dd), 4.55 (1H, s), 4.05-3.88 (3H, m), 3.82 (6H, s), 3.67-3.54 (3H, m), 3.49-3.45 (1H, m), 3.32-3.23 (1H, m), 3.19-2.90 (2H, m), 2.71-2.68 (2H, m), 2.61-2.54 (1H, m), 2.23-2.16 (1H, m), 2.13-2.06 (1H, m), 1.27-1.15 (49H, m), 1.06-0.97 (27H, m). $^{13}$C NMR (CD$_2$Cl$_2$) δ: 160.67, 159.38, 158.61, 154.33, 154.06, 144.96, 136.47, 135.90, 135.79, 130.00, 128.02, 127.76, 126.69, 117.58, 116.77, 113.03, 85.99, 80.69, 80.58, 79.55, 79.49, 76.95, 76.45, 76.36, 64.22, 60.20, 60.12, 59.88, 59.86, 55.16, 49.71, 49.47, 47.77, 47.68, 47.46, 47.26, 45.96, 45.89, 43.99, 43.88, 43.77, 43.65, 28.76, 28.07, 26.39, 26.31, 26.27, 24.87, 24.68, 24.44, 24.37, 24.27, 24.19, 21.90, 21.37, 20.83, 20.76, 20.75, 20.69, 20.35, 20.32, 20.27, 20.24. ESI-MS (m/z): 1165.7203 (M+H)$^+$.

For the synthesis of PMO-DNA chimeras, 5'-DMT-2'-deoxyribonucleoside-3'-phosphoramidite synthons (compounds 26, 27 and 28, FIG. 3A) were prepared following a literature protocol (Roy, et al., J. Am. Chem. Soc. 2013, 135, 6234-6241). Compound 25 of FIG. 3A was obtained from commercially available sources (Glen Research).

General Method for the Synthesis of Compounds 26, 27, and 28 of FIG. 3A

The 5'-dimethoxytrityl-N-BIBS protected 2'-deoxynucleoside was added to a round bottom flask flushed with argon. Anhydrous dichloromethane and 2-cyanoethyl-N,N,N',N'-tetraisopropylphosphorodiamidite (1.2 equivalents) were added via syringe. 1.0 equivalent of tetrazole (0.4 M in CH$_3$CN obtained from Glen Research) was added drop-wise to this solution over one-half hour while stirring. The reaction was stirred at room temperature for 2-3 hours at which time TLC showed complete disappearance of the starting material. The reaction mixture was diluted in dichloromethane and extracted twice with a saturated solution of NaHCO$_3$. The organic layer was dried over Na$_2$SO$_4$, filtered and evaporated to dryness. The product was purified by flash chromatography on a silica column. The silica gel slurry was prepared with the starting eluant mixture containing an additional 5% triethylamine. After pouring the slurry, the column was washed with two column volumes of the starting solvent mixture containing no triethylamine. Compounds 24 and 25 of FIG. 4B were purified using a gradient of 3:7 ethylacetate:hexanes to 1:1 ethylacetate:hexanes. Compound 26 was purified using a 7:3 hexanes:diethylether mixture.

$N^4$-Di(tert-butyl)isobutylsilyl-5'-dimethoxytrityl-2'-deoxycytidine3'-O-cyanoethyl-N,N-diisopropylphosphoramidite (compound 26, FIG. 3A). Yield: 87%. $^{31}$P NMR (CD$_2$Cl$_2$): 148.67, 148.43. $^1$H NMR (CD$_2$Cl$_2$, 400 MHz) δ:7.88-7.80 (1H, dd), 7.49-7.45 (2H, m), 7.37-7.27 (7H, m), 6.90-6.86 (4H, m), 6.35-6.29 (1H, m), 5.53-5.51 (1H, m), 4.71-4.62 (1H, m), 4.49 (1H, bs), 4.20-4.16 (1H, m), 3.89-3.77 (7H, m), 3.72-3.58 (3H, m), 3.51-3.35 (2H, m), 2.68-2.58 (2H, m), 2.52-2.49 (1H, m), 2.30-2.22 (1H, m), 2.11-2.04 (1H, m), 1.29-1.25 (1H, m), 1.23-1.20 (9H, m), 1.14-1.10 (22H, m), 1.02-0.97 (9H, m). $^{13}$C NMR (CD$_2$Cl$_2$) δ:158.71, 155.07, 144.68, 140.67, 135.58, 130.13, 128.15, 127.89, 126.90, 117.75, 117.60, 113.12, 96.04, 86.60, 85.82, 85.77, 85.16, 85.11, 84.98, 84.92, 62.91, 62.61, 58.64, 58.26, 43.30, 43.14, 40.75, 40.53, 28.59, 26.10, 24.79, 24.33, 24.26, 20.66, 20.41, 20.18. ESI-MS (m/z): 928.5201 (M+H)$^+$.

$N^6$-Di(tert-butyl)isobutylsilyl-5'-dimethoxytrityl-2'-deoxyadenosine3'-O-cyanoethyl-N,N-diisopropylphosphoramidite (compound 27, FIG. 3A). Yield: 81%. $^{31}$P NMR (CD$_2$Cl$_2$): 148.51, 148.49. $^1$H NMR (CD$_2$Cl$_2$, 400 MHz) δ: 8.30 (1H, s), 7.98-7.96 (1H, d), 7.47-7.44 (2H, m), 7.37-7.34 (4H, m), 7.31-7.23 (3H, m), 6.87-6.83 (4H, m), 6.46-6.43 (1H, m), 4.86-4.78 (1H, m), 4.34-4.28 (1H, m), 3.92-3.82 (7H, m), 3.78-3.62 (3H, m), 3.47-3.32 (2H, m), 3.02-2.94 (1H, m), 2.70-2.57 (2H, m), 2.55-2.52 (1H, m), 2.18-2.11 (1H, m), 1.25-1.16 (30H, m), 1.10-1.08 (3H, m), 1.03-1.00 (7H, m). $^{13}$C NMR (CD$_2$Cl$_2$) δ: 158.64, 158.09, 152.37, 149.19, 144.86, 138.72, 135.86, 135.67, 130.11, 129.99, 128.09, 127.78, 126.74, 122.27, 117.76, 117.64, 113.05, 86.31, 85.66, 85.45, 84.27, 74.14, 73.97, 73.54, 73.37, 63.67, 63.53, 58.54, 58.26, 43.30, 43.18, 39.03, 38.93, 28.62, 26.25, 26.21, 24.80, 24.42, 24.38, 24.31, 21.02, 20.79, 20.44, 20.37, 20.29, 20.22. ESI-MS (m/z): 952.5279 (M+H)$^+$, 974.5130 (M+Na)$^+$.

$N^2$-Di(tert-butyl)isobutylsilyl-5'-dimethoxytrityl-2'-deoxyguanosine3'-O-cyanoethyl-N,N-diisopropylphosphoramidite (compound 28, FIG. 3A). Yield: 79%. $^{31}$P NMR (CD$_2$Cl$_2$):149.03, 148.52. $^1$H NMR (CD$_2$Cl$_2$, 400 MHz) δ: 7.83-7.77 (1H, d), 7.51-7.48 (2H, m), 7.39-7.24 (7H, m), 6.90-6.86 (4H, m), 6.41-6.38 (1H, t), 4.65-4.60 (1H, m), 4.54 (1H, bs), 4.30-4.28 (1H, m), 3.86-3.76 (7H, m), 3.73-3.61 (3H, m), 3.43-3.33 (2H, m), 2.85-2.45 (4H, m), 2.25-2.17 (1H, m), 2.12-2.05 (1H, m), 1.23-1.15 (48H, m), 1.06-0.97 (18H, m). $^{13}$C NMR (CD$_2$Cl$_2$) δ:160.64, 159.27, 158.67, 154.21, 144.77, 136.28, 135.71, 135.60, 130.08, 128.11, 127.87, 126.80, 117.56, 117.14, 113.13, 86.39, 85.40, 85.09, 83.79, 83.63, 63.78, 63.48, 58.37, 58.16, 43.34, 43.18, 40.88, 40.55, 28.74, 28.09, 26.30, 26.17, 24.89, 24.69, 24.52, 24.45, 24.36, 24.29, 21.90, 21.37, 20.77, 20.73, 20.71, 20.62, 20.40, 20.33, 20.22, 20.15. ESI-MS (m/z): 1188.6903 (M+Na)$^+$.

Example 2

Synthesis of Morpholino Oligonucleotides Using BIBS-Protected Morpholino Phosphoradiamidites Once the synthons described in Example 1 were available, the next goal was to optimize the solid-phase synthesis cycle for preparing borane phosphoroamidate morpholino derivatives, and for converting these compounds to the corresponding PMOs. The synthesis cycle is outlined in FIG. 4 and Table 1. Prior to synthesis, the 5'-DMT group on the 2'-deoxyribothymidine linked to a polystyrene support was removed with 0.5% trifluoroacetic acid in chloroform containing 10% trimethylphosphiteborane (TMPB).

Figure 4B:
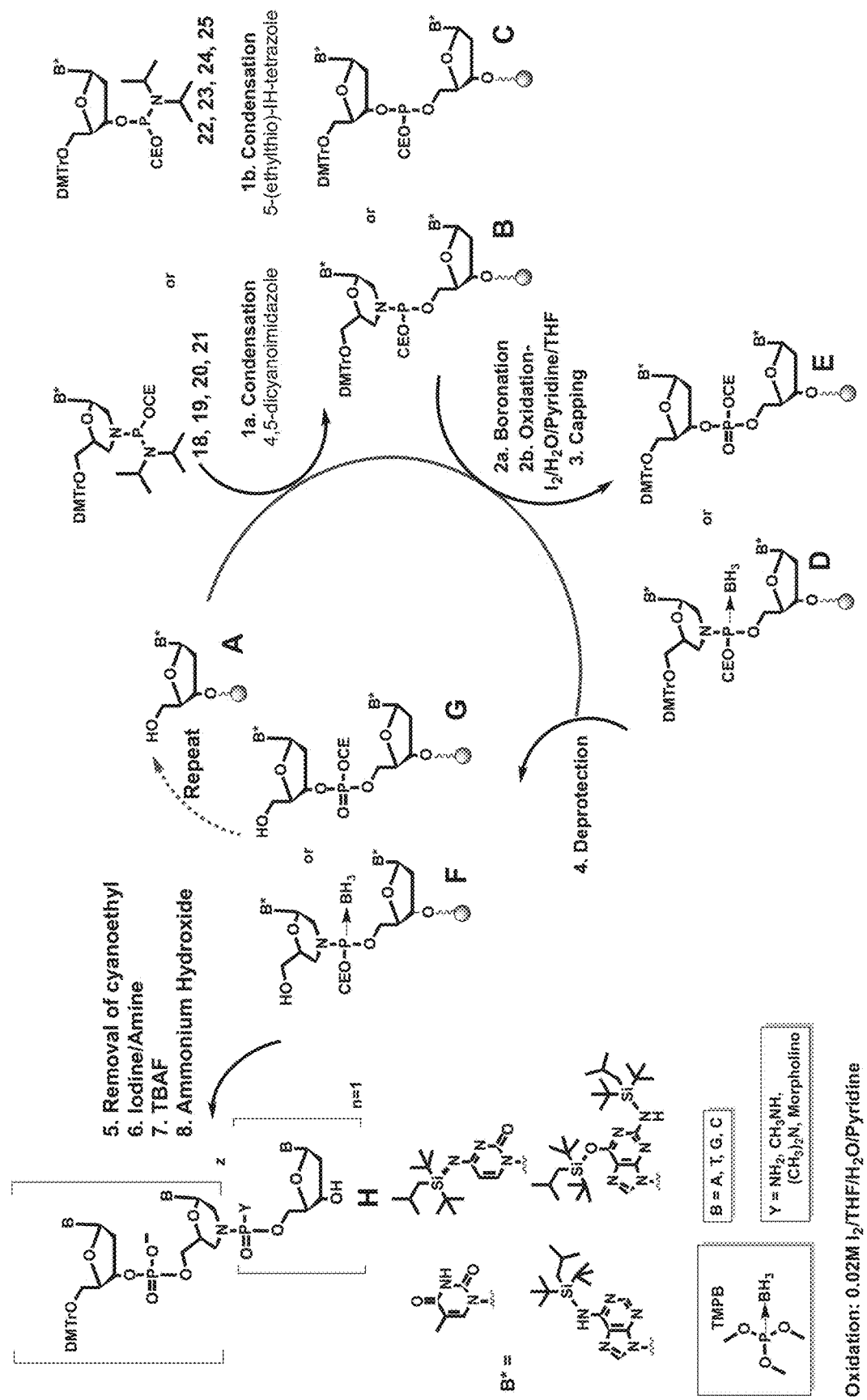
FIG. 4B shows the general synthesis scheme for solid phase synthesis of phosphordiamidate morpholino oligonucleotides (PMOs) having 2'-deoxynucleoside 3'-phosphates (PMO/DNA chimeras) using BIBS-protected phosphoramidites. Compound H is a PMO having a selected number of Y amino groups attached to phosphorus where Y can be any of the amino groups as shown or a large variety of additional amino groups. Compound A is a thymidine 2'-deoxyribonucleoside, but this 2'-deoxyribonucleoside can be replaced by any of the four 2'-deoxyribonucleosides or morpholino nucleosides. For example, when cytosine, adenine, and guanine bases are used, they must be protected with the bis(tertbutyl)isopropylsilyl (BIBS) group.

The 5'-unprotected-2'-deoxyribonucleoside (FIG. 4B, compound A) was allowed to react with one of the synthons (compounds 18, 19, 20, or 21, FIG. 4B) in anhydrous acetonitrile containing 4,5-dicyanoimidazole (DCI) (FIG. 4B, "1. Condensation") to generate a dimer having a phosphoramidite diester internucleotide linkage (FIG. 4B, compound B). The coupling wait time was 300 s. Following boronation, and capping (FIG. 4B, "2. Boronation" and "3. Capping"), and detritylation (FIG. 4B, "4. Deprotection"), repetition of this cycle generates the product ready for further conversion to the PMOs.

TABLE 1

Synthesis cycle for preparing PMOs and PMO-DNA chimeras.

| Reactions | Wash/reagents/solvents | Time (s) |
|---|---|---|
| Detritylation | 10% TMPB + 0.5% TFA in CHCl$_3$ | Flow 45 s |
| Wash | MeOH | Flow 20 s, wait 10 s, flow 10 s. |
| Condensation | 0.1M phosphordiamidite 18, 19, 20, or 21 (in CH$_3$CN) + Activator (0.12M dicyanoimidazole in CH$_3$CN) or | Wait 300 s |
| | 0.1M phosphoramidite 22, 23, 24, or 25 in CH$_3$CN + Activator (0.25M 5-(ethylthio)-1H-tetrazole (ETT) in CH$_3$CN) | Wait 180 s |
| Boronation or Oxidation | 0.05M BH$_3$—THF in THF | Flow 15 s, wait 45 s |
| | 0.02M iodine in THF/water/pyridine | Flow 8 s, wait 15 s |
| Wash | Anhydrous CH$_3$CN | Flow 10 s |
| Capping | Cap A (THF/Pyridine/Ac$_2$O) + Cap B (16% 1-methylimidazole in THF) | Flow 10 s, wait 5 s |
| Wash | Anhydrous CH$_3$CN | Flow 10 s |
| Wash | Anhydrous CH$_2$Cl$_2$ | Flow 25 s |

Post synthesis, supports were washed with acetonitrile, treated with a 1:1 mixture of triethylamine:acetonitrile for 600 s in order to remove the cyanoethyl groups from internucleotide linkages (FIG. 4B, "5. Removal of cyanoethyl"), washed with acetonitrile and dichloromethane several times to remove residual triethylamine, and dried. The polystyrene supports were next removed from columns and placed in 1.5 mL screw-cap glass reaction vials.

To convert the morpholino borane phosphoroamidates to the N,N-dimethylamino PMOs, the morpholino borane phosphoroamidates were treated overnight with a solution of 0.05 M iodine and 2.0 M dimethylamine in tetrahydrofuran (FIG. 4, "6. Iodine/dimethylamine"). The resins were repeatedly washed with acetonitrile, and oligonucleotides were next treated with a 1.0 M solution of tetrabutyl ammonium fluoride (TBAF) in THF to remove the BIBS protecting groups (FIG. 4, "7. Silyl deprotection"). (Et$_3$N.HF could not be used for removing these silyl groups as this reagent hydrolyzed phophorodiamidate linkages).

Figure 4C:
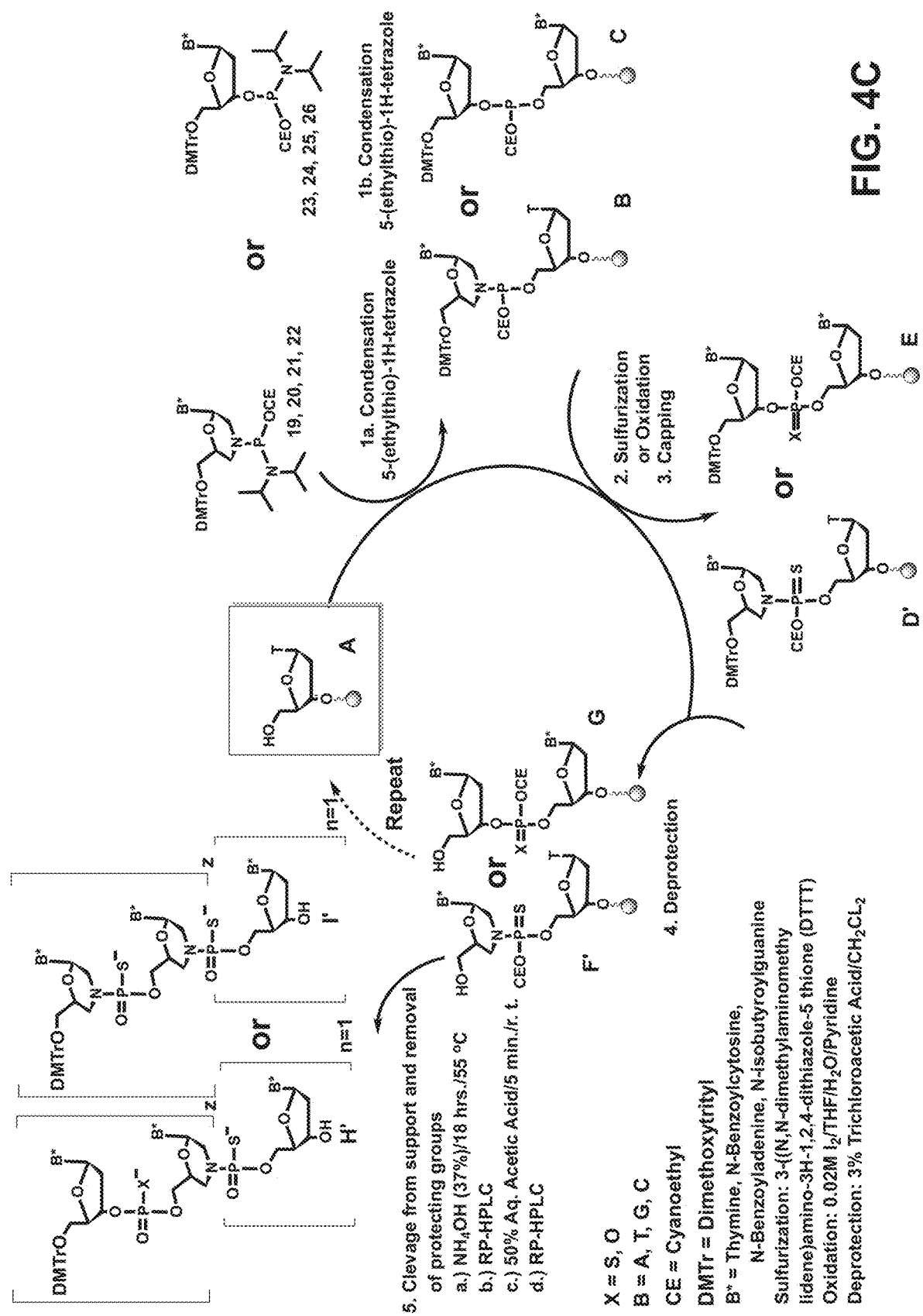
FIG. 4C shows the synthesis scheme for solid phase synthesis of TMO and TMO/DNA oligonucleotides. I' is A TMO having only morpholino nucleosides; H' is a A TMO/DNA chimera having both morpholino and 2'-deoxynucleosides. Compound A is a thymidine 2'-deoxyribonucleoside, but this 2'-deoxyribonucleoside can be replaced by any of the four 2'-deoxyribonucleosides or morpholino nucleosides. For example, when the cytosine, adenine, and guanine bases are used, they must be protected with an appropriate amino protecting group.
Figure 5:
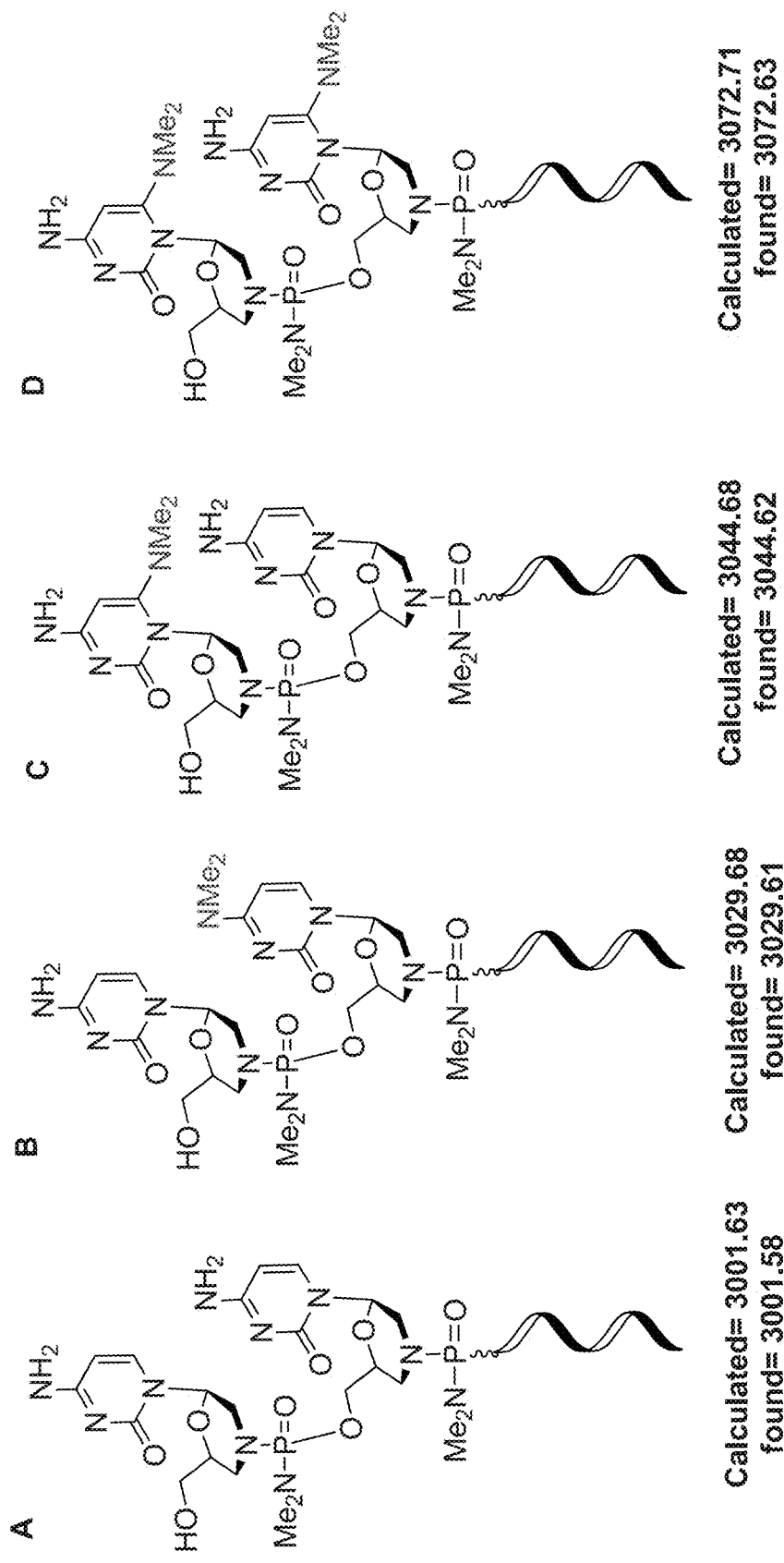
FIG. 5 shows the substitution at the C-4 and C-6 positions of cytosine caused by the use of dimethylamine in the oxidative amination reactions carried out after removal of silyl protecting groups.

When oxidative amination reactions were carried out after removal of silyl protecting groups, amine substitution at the N-4 of cytosine was observed (FIG. 5). This problem was overcome by performing the oxidative amination reaction prior to desilylation, as depicted in FIG. 4, reaction steps 6. and 7.

Once the silyl groups were removed, oligonucleotides were cleaved from supports using 30% ammonium hydroxide (FIG. 4B, "8. Cleavage from support, Ammonium Hydroxide"), polystyrene resins were removed using 0.2 µm centrifugal filters, and solutions were passed through Illustra NAP-25 columns to remove fluoride salts. An additional purification step was performed with each PMO using an Amicon® Ultra-15 3K centrifugal filter device (to remove shorter failure sequences). The oligonucleotides were then used for further characterization and other studies.

This synthesis was carried out on an ABI 394 Synthesizer. All syntheses were performed at a 0.2 micromol scale using a 5'-DMT 2'-deoxythymidine joined to a low volume polystyrene solid support via a succinate linkage. For synthesis of morpholino oligonucleotides, a standard 0.2 micro mole synthesis cycle was used with an increased coupling time of 300 s. A wash with methanol followed the detritylation step. All the phosphordiamidites (compounds 18, 19, 20, or 21 of FIG. 4B; 0.1 M) were dissolved in anhydrous CH$_3$CN. Detritylation was carried out using a 0.5% solution of TFA in anhydrous CHCl$_3$ containing 10% TMPB. Solutions for boronation (0.05 M BH$_3$-THF complex in THF) were prepared fresh prior to use. Reagents for activation (4,5-dicyanoimidazole) and capping were purchased form Glen Research. A stepwise description of the synthesis cycle is described in Table 1. Deprotection was carried out in two steps: the solid support-linked borane-phosphoramidate morpholino oligonucleotides were first treated with a 1:1 solution of triethylamine in acetonitrile for 10 minutes followed by extensive washing with acetonitrile. The resin was then dried using a flow of argon and transferred to a glass vial. A solution of iodine (0.05M) and dimethyl amine in THF (2.0 M) was added to the glass vial. For reactions with ammonia, an identical amount of iodine was dissolved in a solution of ammonia (2.0 M) in isopropanol and this solution was added to the resin. The glass vial was then placed on a mechanical shaker for 24 hrs. For the synthesis of the methylamine and morpholinodiamidate derivatives, a 2.0 M solution of each amine in THF was used.

The vials containing resins were centrifuged at 4000 rpm and the supernatants removed with a pipette. Subsequently, resins were washed 4-5 times with 2 mL aliquots of acetonitrile, shaken vigorously, placed in a centrifuge at 4000 rpm for 5 minutes and supernatants removed. For amino-modified morpholino derivatives, the ammonia solution in isopropanol was removed under vacuum. These morpholino oligonucleotides were desilylated by overnight fluoride (1.0 mL of 1.0 M solution of tetrabutylammonium fluoride in THF) treatment. The resins were then treated with 1 mL of 37% ammonium hydroxide in water for 1 h in order to remove the product from the resins and the polystyrene resin beads were removed using a 0.2 µm centrifugal filter.

The total volume of each solution was diluted to 2.5 mL by adding 0.5 mL Milipore water and the PMOs were desalted using Illustra™ NAP™-25 Columns (GE Healthcare). Initially, these columns were equilibrated with 25.0 mL of water. After allowing water to completely enter the gel beds by gravity flow, 2.5 mL of samples were loaded onto columns and the purified samples were eluted using 3.5 mL Milipore water. Second step purifications were carried out for oligonucleotides having more than 10 nucleotides by using AMICON® Ultra-4 3K devices. Solutions that accumulated after Nap column purification (3.5 mL total volume) were loaded on to Amicon devices and centrifuged at 4000×g for 30 minutes. Concentrated solutes were washed with 3.0 mL×2 of Milipore water in similar fashion. The oligonucleotides were collected and used for various experiments.

Incorporation of the uridine morpholino phosphordiamidite (similar to compound 18 of FIG. 4B, except B*=uracil) into siRNA sequences by means of 5-(ethylthio)-1H-tetrazole (ETT) and subsequent conversion of the resulting morpholino phosphoramidite internucleotide linkage to the corresponding phosphoramidate morpholino linkage with aqueous iodine has been reported (Tetrahedron Letters 2008, 49:3570-73; Bioorg. Med. Chem., 2009, 17:2441-46). But the current inventors found that ETT ($pK_a$=4.3) activated both morpholine and N,N-diisopropylamine in compounds 18, 19, 20, or 21 of FIG. 4B. Consequently, very low yields of the final PMO products were observed following those literature protocols, because activation of the morpholine followed by boronation and iodine/dimethylamine oxidation, leads to a capped PMO oligonucleotide having a 5'-N,N-diisopropylamino-phosphorodiamidate that cannot be further elongated. In order to further investigate this problem, several less acidic activators (tetrazole, saccharin-1-methylimidazole, 4,5-dicyanoimidazole) were tested to identify one that would react with N,N-diisopropylamine ($pK_a$=11.1), but would react only minimally with morpholine ($pK_a$=8.3). Of the activators screened in synthesizing PMOs having a sequence corresponding to ODN1 (Table 2), 4,5-dicyanoimidazole ($pK_a$=5.2, 0.12 M, with 300 s coupling time) generated the highest yield (67%) of the desired PMO with low levels of side-products. Because the morpholino phosphoramidite diester synthesized following the coupling step (FIG. 4A, compound B), was unstable towards the capping solution, boronation was carried out in order to generate a phosphorus (IV) morpholino compound (FIG. 4A, compound D) prior to the capping step. After boronation, the support was washed with acetonitrile, failure sequences were capped using acetic anhydride, and detritylation was carried out using a solution of 10% TMBP and 0.5% TFA in chloroform (compound D of FIG. 4A was stable to these acidic detritylation conditions).

Figure 6:
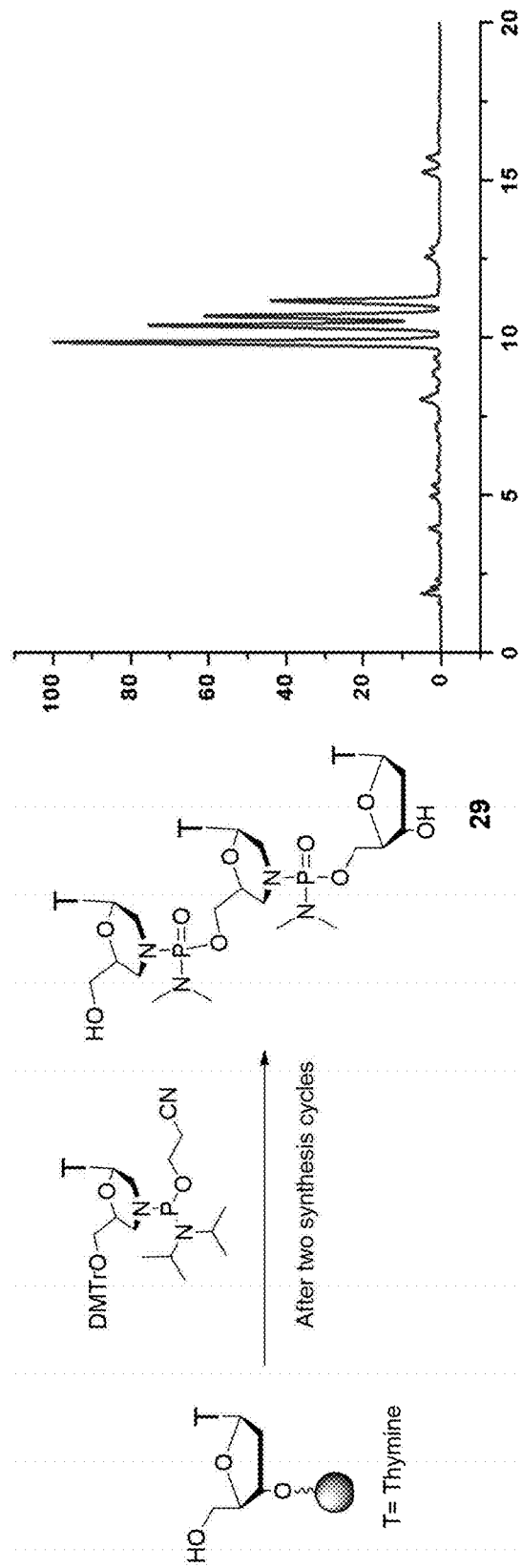
FIG. 6 depicts the synthesis of a N,N-Dimethylamino PMO trimer (left panel), and the LC profile from the LCMS analysis of the total reaction mixture (right panel).
Figure 7C:
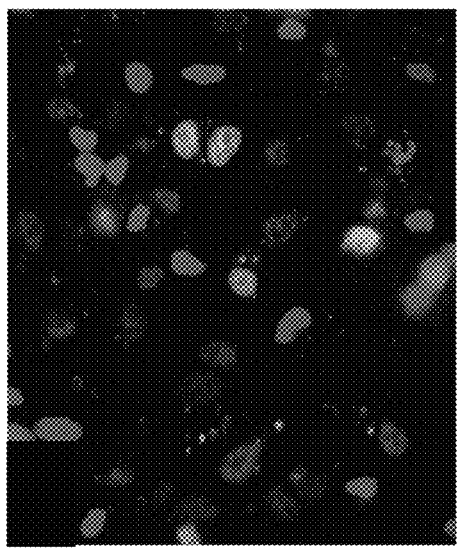
FIGS. 7A-7F show fluorescence microscopy visualization of ODN 27 transfection. ODN 27 (100 nM) in reduced serum medium (Opti-MEM) was transfected into HeLa cells using Dharmafect 1, followed by 18 h of incubation at 37° C. Cells were then washed with PBS and fixed using buffered formalin solution. Nuclei of the cells were counterstained with DAPI.
Figure 7F:
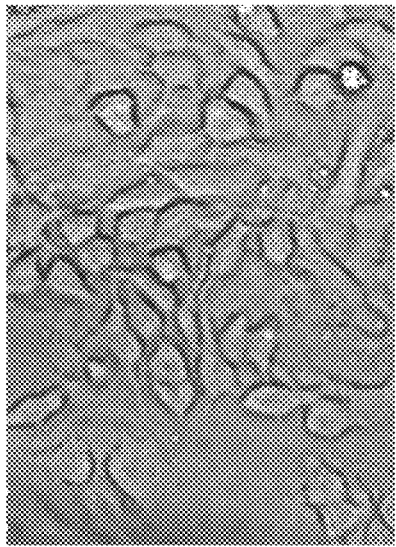
Figure 7B:
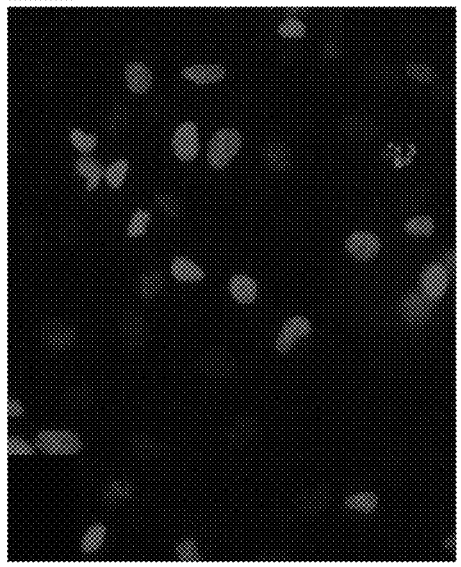
Figure 7E:
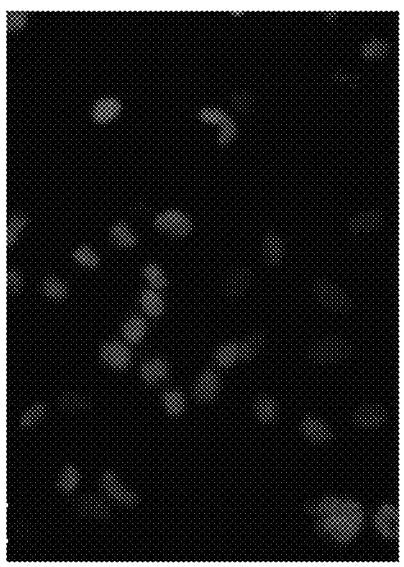
Figure 7A:
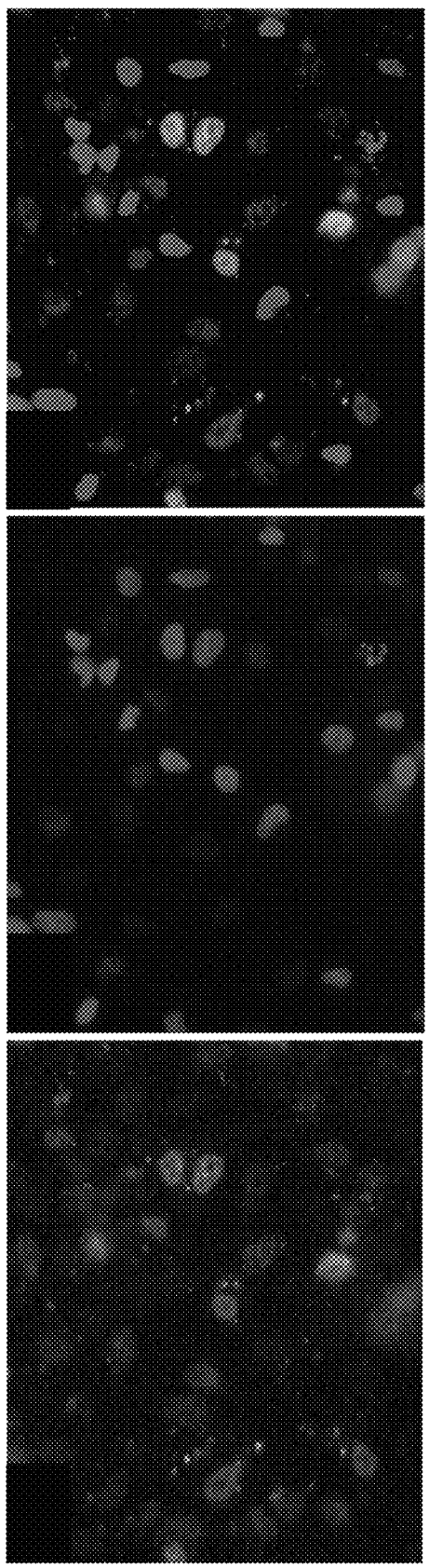
Figure 7D:
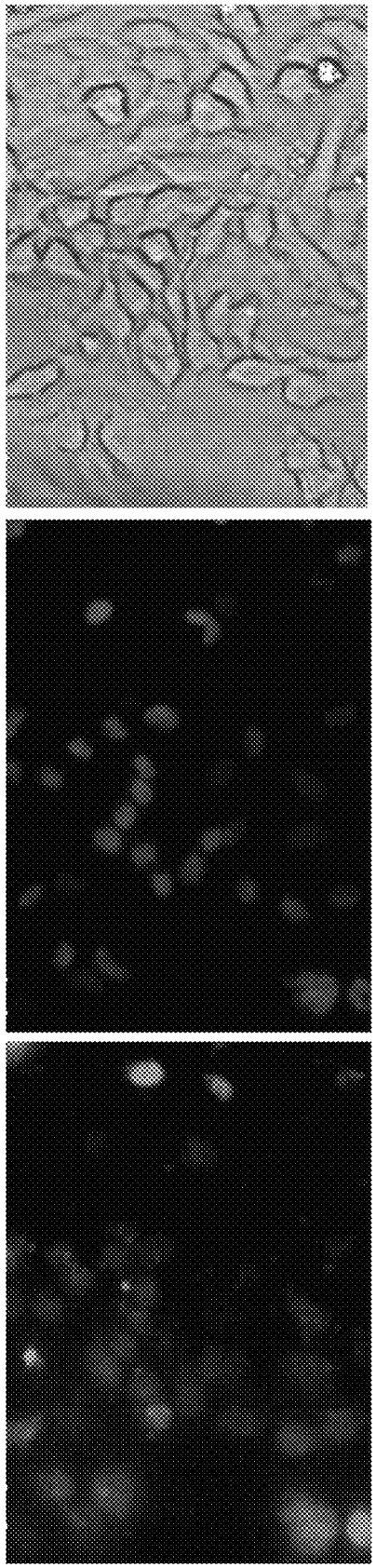

Using this synthesis procedure outlined in FIG. 4, a trimer having only thymine nucleoside bases was synthesized, converted to the N,N-dimethylamino PMO derivative with iodine/N,N-dimethylamine, removed from the support with ammonia, and analyzed by LCMS. The four major peaks as shown in the LC profile (FIG. 6, right panel) have the mass spectra expected for the four diastereomers of the product (calculated mass, 902.3, found 901.3). A 94% yield of the product was calculated when the combined areas of all peaks from the crude reaction mixture were compared to the peak area for these diastereomers. In a similar experiment in which a dimer was prepared, the first coupling yield was found to be 96%, which is far better than other reported procedures (Bioorg. Med. Chem. Lett. 2012, 22:1445-47; Tetrahedron Letters, 2015, 56; 4565-68).

TABLE 2

Mass analysis (LCMS) of PMO and PMO-DNA chimeras (ODNs). Oligonucleotides containing N,N-dimethylamino-phosphorodiamidate (*) and phosphate (p) internucleotide linkages are shown. Morpholino and 2'-deoxyribonucleosides are shown as upper and lower case letters respectively.

| NO | ODNs | Mol wt Cal | Mol wt Obs |
|---|---|---|---|
| ODN 1 | T*T*T*T*T*T*T*T*T*t | 3214.00 | 3214.01 |
| ODN 2 | T*T*T*T*T*T*T*T*T*T*T*T*T*T*T*T*T*T*t | 6846.17 | 6848.14 |
| ODN 3 | C*C*C*T*T*T*T*T*T*T*t | 3829.36 | 3828.16 |
| ODN 4 | A*A*A*T*T*T*T*T*T*T*t | 3901.44 | 3902.30 |
| ODN 5 | G*G*T*T*T*T*T*T*T*T*t | 3924.42 | 3925.26 |
| ODN 6 | G*A*C*T*T*T*T*T*T*T*t | 3893.41 | 3894.25 |
| ODN 7 | A*T*G*T*G*C*T*G*C*T*A*t | 3937.44 | 3938.28 |
| ODN 8 | T*A*A*C*A*C*G*A*T*A*C*G*C*G*A*t | 5264.26 | 5264.75 |
| ODN 9 | T*T*T*T*$t_p$ $t_p$ $t_p$ $t_p$ $t_p$ $t_p$ $t_p$ $t_p$ $t_p$ $t_p$ $t_p$ $t_p$ $t_p$ $t_p$ t | 6430.17 | 6430.15 |
| ODN 10 | $t_p$ $t_p$ $t_p$ $t_p$ $t_p$ $t_p$ $t_p$ $t_p$ $t_p$ $t_p$ $t_p$ $t_p$ $t_p$ $t_p$ $t_p$ T*T*T*T*t | 6430.17 | 6430.15 |
| ODN 11 | $t_p$ $t_p$ $t_p$ $t_p$ $t_p$ $t_p$ $t_p$ $t_p$ T*T*T*T*$t_p$ $t_p$ $t_p$ $t_p$ $t_p$ $t_p$ $t_p$ t | 6430.17 | 6430.14 |
| ODN 12 | T*T*T*T*$t_p$ $t_p$ $t_p$ $t_p$ $t_p$ $t_p$ $t_p$ $t_p$ $t_p$ $t_p$ T*T*T*T*t | 6534.17 | 6534.38 |
| ODN 13 | T*$t_p$ $t_p$ T*$t_p$ $t_p$ T*$t_p$ $t_p$ T*$t_p$ $t_p$ T*$t_p$ $t_p$ T*t | 6482.26 | 6482.17 |
| ODN 14 | $t_p a_p g_p t_p t_p g_p a_p g_p t_p g_p a_p t_p$ A*T*C*A*t | 5343.45 | 5343.07 |
| ODN 15 | G*T*A*G*$t_p c_p c_p t_p g_p c_p a_p a_p t_p g_p a_p$ t | 5000.26 | 4999.99 |
| ODN 16 | T*G*A*$t_p c_p g_p c_p t_p g_p c_p a_p a_p$ T*G*A*t | 5052.26 | 5052.16 |

N,N-Dimethylamino PMOs having oligothymidine (Table 2, ODNs 1 and 2) and all four bases (Table 2, ODNs 3-8), were synthesized using this approach and characterized by LCMS. Because it has been established that PMOs 12-16 nucleosides in length are effective inhibitors of RNA expression (either via blockage of splicing or blockage of mRNA translation), the inventors next carried out the synthesis of a 16-mer having all four bases (Table 2, ODN 8). The LCMS chromatogram of the unpurified reaction mixture showed that both the yield (10 $A_{260}$ units isolated) and mass analysis of this ODN were satisfactory.

Example 3

Synthesis of PMO-DNA Chimeras

For the synthesis of PMO-DNA chimeras, 4,5-dicyanoimidazole (0.12 M and 300 s coupling time) and ETT (0.25 M and 180 s coupling time) were used for the morpholino phosphordiamidate synthons (compounds 18, 19, 20, or 21 of FIG. 4B), and the 5'-dimethoxytrityl-2'-deoxyribonucleoside-3'-phosphoramidites (compounds 22, 23, 24 or 25 of FIG. 4B), respectively. Following condensation, a morpholino phosphoramidite diester was converted to the phosphorus (IV) borane linkage and standard oxidation with 0.02 M iodine in THF/water/pyridine was used to convert a phosphite triester to the phosphate triester. These synthesis steps were repeated until the PMO-DNA chimeras of the desired sequence/length were prepared. Table 1 summarizes these synthesis steps.

Because PMO-DNA chimeras are new to the scientific community and could prove to be useful for various research projects, several were synthesized (Table 2, ODNs 9-16). Initially these chimeras were prepared as a series of 21-mer oligothymidines containing four N,N-dimethylamino PMO linkages. In these 21-mers, the morpholino diamidate linkages were placed adjacent to either the 5' or 3' ends, or near the middle of the 21mer, and at every third position throughout the oligomer (Table 2; ODNs, 9, 10, 11, 12 and 13). For these chimeras, substitution of borane with dimethylamine upon activation by iodine proceeded efficiently and analysis of the crude reaction mixtures by LCMS revealed that the expected phosphorodiamidate linkages were formed in near quantitative yields. These encouraging results were followed by the synthesis of PMO-DNA chimeras containing all four nucleobases with variable locations and number of PMO linkages (Table 2: ODNs, 14, 15, and 16). LCMS analysis and $31^P$ NMR of the reaction mixtures demonstrated that the expected PMO-DNA chimeras were obtained in high yields with an average yield being 10-20 A260 units (from a 0.2 µM synthesis cycle). These experiments also demonstrated that treatment with dimethylamine does not lead to measurable cleavage of the succinate linkage and loss of product during synthesis.

Example 4

Solid Phase Synthesis of PMOs with Amino, N-Methylamino and Morpholino Linkages It is known that boranephosphonate linkages can be activated with iodine for displacement by a large number of nucleophiles. Therefore in addition to testing this new synthetic route by synthesizing PMO analogues having the N,N-dimethylamino-phosphorodiamidate linkage, we decided to investigate whether other amines could be used in order to generate several new PMO-DNA derivatives.

Initially, an oligothymidine 21-mer having four boranephosphoramidate morpholino linkages near the center of this oligomer was synthesized. The support containing this oligonucleotide was divided into three samples that were treated with N-methylamine, ammonia, and morpholine under iodine oxidation conditions and then purified using reverse phase column chromatography. Additionally, mixed sequence PMO-DNA chimers having all four bases and amino-phosphorodiamidate internucleotide linkages were synthesized where the positions for the diamidate linkages were located at the 5', 3', and 5'/3' termini of these chimeras. The sequence and mass analysis from LCMS of these PMOs are listed in Table 3. Yields were comparable to those obtained for the N,N-dimethylamino PMO chimeras.

TABLE 3

LCMS Analysis of PMO-DNA Chimeras. ODN 17, 20, 21and 22: * = $NH_2$; ODN 18: ♦ = NHMe; ODN 19: • = morpholine. Phosphate linkages are denoted by "p". Morpholino and 2'-deoxyribonucleosides are noted as upper and lower case letters respectively.

| | | Mol wt | |
|---|---|---|---|
| NO | ODNs | Cal | Obs |
| ODN 17 | t$_p$t$_p$t$_p$t$_p$t$_p$t$_p$t$_p$T*T*T*T*t$_p$t$_p$t$_p$t$_p$t$_p$t$_p$t$_p$t | 6318.21 | 6318.02 |
| ODN 18 | t$_p$t$_p$t$_p$t$_p$t$_p$t$_p$t$_p$T♦T♦T♦T♦t$_p$t$_p$t$_p$t$_p$t$_p$t$_p$t$_p$t | 6374.32 | 6374.08 |

TABLE 3-continued

LCMS Analysis of PMO-DNA Chimeras. ODN 17, 20, 21and 22: * = $NH_2$; ODN 18: ♦ = NHMe; ODN 19: • = morpholine. Phosphate linkages are denoted by "p". Morpholino and 2'-deoxyribonucleosides are noted as upper and lower case letters respectively.

| | | Mol wt | |
|---|---|---|---|
| NO | ODNs | Cal | Obs |
| ODN 19 | t$_p$t$_p$t$_p$t$_p$t$_p$t$_p$t$_p$T•T•T•T•t$_p$t$_p$t$_p$t$_p$t$_p$t$_p$t$_p$t | 6598.57 | 6598.20 |
| ODN 20 | t$_p$a$_p$g$_p$t$_p$t$_p$g$_p$a$_p$g$_p$t$_p$g$_p$a$_p$t$_p$A*T*C*A*t | 5231.48 | 5230.97 |
| ODN 21 | G*T*A*G*t$_p$c$_p$c$_p$t$_p$g$_p$c$_p$a$_p$a$_p$t$_p$g$_p$a$_p$t | 4888.26 | 4887.89 |
| ODN 22 | T*G*A*t$_p$c$_p$g$_p$c$_p$t$_p$g$_p$c$_p$a$_p$a$_p$T*G*A*t | 4884.26 | 4883.96 |

Example 5

Melting Temperatures of PMO-DNA Chimeras

To assess the target binding ability of the modified PMO-DNA chimeras, duplex hybridization studies were performed with 2'-deoxyoligothymidines having amino, methylamino, morpholino, and dimethylamino-morpholino internucleotide linkages. PMOs 11, 17, 18 and 19 were mixed with 2'-deoxyribo-, or riboadenosine-oligonucleotides that were 21-nucleotides in length, in a 1:1 ratio in a buffer (1.0 M NaCl, 10 mM sodium phosphate, pH 7.1) at an overall concentration of 1.0 µM of duplex. The samples were denatured at 90° C. and cooled to 15° C. They were then heated at a rate of 1° C./min, and $A_{260}$ versus time was recorded. Melting temperatures were taken as the temperature of half dissociation and were obtained from the first derivative plots (Table 4).

Melting temperature studies of RNA heteroduplexes with PMOs 11, 17, 18, and 19 showed that introduction of phosphorodiamidate internucleotide linkages stabilized the PMO:RNA duplex relative to the unmodified duplex. The trend in increased stabilization was amino>N-methylamino>N,N-dimethylamino>morpholino. When the PMO-DNA chimeras were allowed to form duplexes with a 2'-deoxyriboadenosine 21mer, a similar trend was observed when compared to the Tm of the unmodified DNA.DNA duplex, except for the morpholino analogue.

TABLE 4

Tm Results with PMO-DNA Chimeras. PMO-DNA chimeras (ODNs 11, 17, 18, and 19), and unmodified ODN 23, (d(T)$_{21}$), were mixed with complementary d(A)$_{21}$ or r(A)$_{21}$ and the melting temperatures measured (Supplementary Section).

| | | $T_m{}^a$(° C.) | | $\Delta T_m{}^b$(° C.) | |
|---|---|---|---|---|---|
| Number | Modification | DNA | RNA | DNA | RNA |
| ODN 23 | — | 58.47 | 51.13 | — | — |
| ODN 11 | $NMe_2$ | 58.37 | 52.42 | 0.025 | 0.32 |
| ODN 17 | $NH_2$ | 61.37 | 53.37 | 0.75 | 0.56 |
| ODN 18 | NHMe | 59.03 | 52.17 | 0.14 | 0.26 |
| ODN 19 | 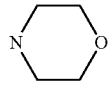 | 57.37 | 51.37 | −0.27 | 0.06 |

$^a T_m$ measurements represent an average of at least three experiments.
$^b \Delta T_m$ represents ($T_m$ ODN-$T_m$ unmodified control)/number of modifications).

Example 6

RNase H1 Activity of Chimeric PMO-RNA Heteroduplexes

N,N-Dimethylamino PMO-DNA chimeras were tested for their ability to stimulate RNase H1 activity. The test systems were composed of a 5'-O-fluorescein-labeled RNA and complementary N,N-dimethylamino PMO-chimeras.

Synthesis of a 5'-Fluorescein PMO-DNA Chimera.

After completion of a DMT-ON synthesis of the boranephosphoramidate morpholino chimera, the ODN was conjugated with 5'-Amino-Modifier C6-TFA (Glen research) using a standard DNA synthesis cycle. After carrying out the iodine oxidation reaction and desilylation of exocyclic amines, the oligonucleotide was purified using reverse phase HPLC (Buffer A: triethylammonium bicarbonate, 0.05 M, Buffer B: acetonitrile; 0-100% B in 50 mins; 55° C.; 4.0 mL/min flow rate). The purified ODN was dissolved in 1 mL of a solution of 1:1 NH$_4$OH:CH$_3$NH$_2$ and heated at 65° C. for three hours to remove the trifluroacetamido group. The reaction mixture was dried and dissolved in a buffer (200 microL) containing 20 mM sodium phosphate and 0.15 M NaCl (pH 8.0) and the concentration was measured. A 20 fold molar excess of 5-(and 6-)carboxy-fluorescein succinimidyl ester (Thermo Fisher Scientific) was dissolved in DMSO and added to the ODN solution. The reaction mixture was stirred at room temperature for 1 h followed by stirring at 4° C. for a period of 3 h. The reaction mixture was diluted using 300 microL water and excess NHS-fluorescein was removed using ILLUSTRA™ NAP™-5 Column. The analyzed PMOs were oligothymidine 14-mers with cap/gap sequences (ODNs 24-26, Table 5) having N,N-dimethylamino PMO linkages on either end and 3-7 phosphodiester linkages in the center of the analogues. Controls were complementary DNA, and 2'-O-methyl RNA (which activate, and do not stimulate RNase H1 activity, respectively). All these cap/gap oligonucleotide analogues were found to activate RNA hydrolysis.

Hydrolysis of RNA Heteroduplexes with *E. coli* RNase H1.

Experiments with *E. coli* RNaseH1 (Promega) were performed using previously-described conditions (*J. Am. Chem. Soc.*, 2003, 125:940-50). The reactions were carried out using an assay buffer of 50 mM tris-HCl (pH 8.0), 20 mM KCl, 9 mM MgCl$_2$, 1 mM β-mercaptoethanol, and 250 µg/mL bovine serum albumin. An oligodeoxynucleotide or modified oligodeoxynucleotide (200 pmol) and 5'-O-fluorescein-labeled, complementary oligoribonucleotide were added to the assay buffer (35 µL). Following the addition of *E. coli* RNase H1 (3 units), reactions were carried out at 25° C. over 12 h. The reaction mixtures were diluted with an equal volume of 80% formamide gel loading buffer containing tracking dyes and analyzed by polyacrylamide gel electrophoresis (20%, 19:1 cross-linking, 7 M urea). All reactions were performed in triplicate. The developed gels were analyzed using a Molecular Dynamics Typhoon Phosphorimager.

TABLE 5

PMO-DNA Chimeras Used for RNaseH1 assays. Oligonucleotides containing N,N-dimethylaminophosphorodiamidate (*) and phosphate (p) linkages are shown. Morpholino and 2'-deoxynucleosidesare noted by upper and lower case letters respectively.

| ODN | ODNs | Mol wt Cal | Mol wt Obs |
|---|---|---|---|
| ODN 24 | T*T*T*T*T*T$_p$T$_p$T$_p$T*T*T*T*t | 4456.79 | 4457.29 |
| ODN 25 | T*T*T*T*T$_p$T$_p$T$_p$T$_p$T$_p$T*T*T*T*t | 4404.81 | 4405.14 |
| ODN 26 | T*T*T*T$_p$T$_p$T$_p$T$_p$T$_p$T$_p$T$_p$T*T*T*t | 4352.91 | 4353.01 |

Example 7

Cellular Uptake

Because uncharged PMOs cannot be delivered to cells using lipid-based transfection reagents, the cellular uptake of these PMO-DNA chimeras was investigated in the presence of Dharmafect 1, a commonly used siRNA transfection reagent. A PMO-DNA chimera was synthesize (ODN 27, 5'-FL-T*G*T*A*a$_p$a$_p$c$_p$c$_p$a$_p$t$_p$g$_p$a$_p$t$_p$g$_p$t$_p$g$_p$c$_p$t$_p$G*C*T*A*t, See Table 2 for a description of these abbreviations) where the internal, normal nucleotides were flanked at the 5'- and 3'-ends with N,N-dimethylamino PMO nucleotides. ODN 27 also contained a fluorescein dye (FL) joined by a six-carbon linker. HeLa cells were transfected with ODN 27 (100 nM concentration) in the presence of Dharmafect 1 with live cells and fixed cells (FIG. 7) imaged by fluorescent microscopy after 20 h and 18 h incubation, respectively.

Lipid Transfection as Observed by Microscope Imaging.

An ODN 27 stock solution was diluted with 200 microL OptiMEM to a final concentration of 0.1 microM ODN. In a separate Eppendorf Tube, 5.0 microL DharmaFECT 1 was diluted with 200 microL OptiMEM. The 200 microL solution of ODN 27 and the DhamaFECT 1 solution were mixed, equilibrated for 20 min, and 600 microL OptiMEM was added. Hela cells were seeded at 0.3×10$^6$ cells/well on a coverslip placed in a six well plate in DMEM medium containing 10% FBS and penstrep. After 24 hours, medium was removed and the cells were washed twice (2.0 mL D-PBS/wash) before transfection at 80% confluency. D-PBS was removed from the HeLa cells, and 1.0 mL of the transfection mixture was added to each well. Cells were then incubated at 37° C. for 18 hours and washed twice (2.0 mL D-PBS/wash). Cells were covered with 1.0 mL of 10% neutral buffer formalin for 15 mins. The formalin solution was removed and the cells were covered with 3.0 mL DPBS for 10 min at RT. The coverslips were removed from the wells and mounted upside down on coverslides using Flouromount-G with DAPI as mounting media and observed using an inverted microscope (OlympuslX 81) equipped with a Hamamatsu C4742-95 CCD and CoolSNAP ES digital camera.

The transfection was dose dependent as an increased fluorescent signal was observed when cells were incubated with 100 nM of ODN 27. The fluorescence appears to be distributed primarily in the nucleus although there is also evidence of cytoplasmic distribution without the common punctuated structures found for many analogues.

Example 8

Synthesis of Phosphoramidite Monomers for Thiomorpholino Synthesis

The general procedure for the synthesis of phosphoramidite monomers (compounds 19, 20, 21, and 22 of FIG.

4C) is depicted in the synthesis scheme of FIG. 3B where cytosine, adenine, and guanine exocyclic amines are protected with base-labile or other appropriate protecting groups. Briefly, 5'-O-DMT-protected morpholino nucleosides (compounds 15, 16, 17, or 18 of FIG. 3B) were dried overnight in vacuum, and dissolved in anhydrous $CH_2Cl_2$ followed by the addition of 1.2 equivalents of 2-cyanoethyl-N,N,N',N'-tetraisopropyl-phosphorodiamidite under argon. After adding 0.5 equivalent of 4,5-dicyano imidazole, the reaction was allowed to stir under argon atmosphere at room temperature when TLC indicates complete conversion of starting material. As described above, the silica gel slurry was prepared with the starting eluant mixture containing an additional 5% triethylamine. After pouring the slurry, the column was washed with two column volumes of the starting solvent mixture containing no triethylamine. Compounds 19, 20, 21, and 22 of FIG. 3B were purified using a gradient of 3:7 ethylacetate:hexanes to 9:1 ethylacetate: hexanes.

5'-dimethoxytrityl-morpholinothymidine-3'-N-cyanoethyl-N,N diisopropyl phosphoradiamidite (compound 19 of FIG. 3B): Yield: 76%. $^{31}P$ NMR. $^1H$ NMR ($CD_2Cl_2$, 400 MHz) δ: 9.51 (1H, bs), 7.50-7.47 (2H, m), 7.38-7.25 (8H, m), 6.89-6.86 (4H, m), 5.78-5.75 (0.5H, dd), 5.65-5.62 (0.5H, dd), 4.08-4.02 (1H, m), 3.99-3.86 (3H, m), 3.82 (6H, s), 3.65-3.52 (2H, m), 3.48-3.34 (1H, m), 3.31-3.27 (1H, m), 3.13-3.09 (1H, m), 2.75-2.68 (2H, m), 2.53-2.47 (2H, m), 1.96 (3H, m), 1.25-1.18 (12H, m). $^{13}C$ NMR ($CD_2Cl_2$) δ: 164.02, 163.96, 158.66, 150.13, 144.95, 135.92, 135.90, 135.79, 135.68, 135.52, 129.99, 128.07, 127.77, 126.77, 117.89, 117.74, 113.05, 110.48, 110.39, 86.05, 80.54, 80.49, 80.20, 77.36, 77.21, 64.37, 60.09, 59.84, 55.20, 49.05, 48.83, 47.58, 47.06, 46.83, 45.87, 45.78, 43.91, 43.74, 24.36, 24.29, 24.22, 24.20, 20.77, 20.33, 20.66, 12.29. ESI-MS (m/z): 727.4047 $(M+H)^+$.

$N^4$-benzoyl-5'-dimethoxytrityl-morpholinocytidine-3'-N-cyanoethyl-N,N-diisopropyl phosphoradiamidite (compound 20 of FIG. 3B): Yield:60%. $^{31}P$ NMR. $^1H$ NMR ($CD_2Cl_2$, 400 MHz) δ: 7.99-7.96 (3H, m), 7.67-7.64 (1H, m), 7.56-7.49 (5H, m), 7.39-7.26 (7H, m), 6.89-6.87 (4H, m), 5.83-5.67 (1H, m), 4.11-4.07 (1H, m), 4.09-3.87 (2H, m), 3.83 (6H, s), 3.81-3.77 (1H, m), 3.65-3.48 (3H, m), 3.37-3.25 (2H, m), 3.19-3.15 (1H, m), 2.78-2.75 (1H, m), 2.72-2.68 (1H, m), 2.56-2.53 (1H, m), 2.39-2.33 (1H, m), 1.25-1.18 (12H, m). $^{13}C$ NMR ($CD_2Cl_2$) δ: 162.22, 158.65, 144.94, 135.92, 135.78, 133.01, 130.05, 130.00, 128.89, 128.06, 127.80, 127.64, 126.79, 117.91, 117.77, 113.05, 86.04, 82.17, 81.93, 77.36, 64.40, 60.22, 60.11, 59.87, 49.85, 49.62, 48.22, 48.17, 47.05, 46.81, 45.70, 45.63, 43.94, 43.88, 43.82, 43.77, 24.38, 24.30, 24.24, 24.16, 20.34, 20.30, 20.22. ESI-MS (m/z): 833.3801 $(M+H)^+$.

$N^6$-benzoyl-5'-dimethoxytrityl-morpholinoadenosine-3'-N-cyanoethyl-N,N-diisopropyl phosphoradiamidite (compound 21 of FIG. 3B): Yield:62%. $^{31}P$ NMR. $^1H$ NMR ($CD_2Cl_2$, 400 MHz) δ: 9.15 (1H, s), 8.78 (1H, s), 8.25-8.24 (1H, d), 8.03-8.01 (2H, m), 7.67-7.63 (1H, m), 7.58-7.54 (2H, m), 7.51-7.47 (2H, m), 7.38-7.24 (7H, m), 6.04-5.90 (1H, m), 4.18-4.11 (1H, m), 4.09-4.05 (1H, m), 4.00-3.89 (2H, m), 3.86 (1H, bs), 3.83 (6H, s), 3.70-3.54 (3H, m), 3.42-3.31 (2H, m), 3.19-3.15 (1H, m), 2.99-2.89 (1H, m), 2.77-2.74 (1H, m), 2.72-2.62 (2H, m), 1.27-1.21 (12H, m). $^{13}C$ NMR ($CD_2Cl_2$) δ: 158.64, 152.41, 152.32, 149.56, 144.92, 140.71, 135.86, 135.74, 134.02, 132.60, 130.00, 128.79, 128.04, 127.78, 126.77, 123.19, 123.11, 117.81, 117.74, 113.04, 86.08, 80.81, 80.60, 77.15, 64.27, 60.14, 59.80, 50.27, 50.04, 48.66, 47.29, 47.06, 45.97, 43.92, 43.72, 24.24, 24.19, 20.29. ESI-MS (m/z): 857.3911 $(M+H)^+$.

$N^2$-isobutyryl-5'-dimethoxytrityl-morpholinoguanosine-3'-N-cyanoethyl-N,N-diisopropyl phosphoradiamidite (compound 22 of FIG. 3B): Yield: 33%. $^{31}P$ NMR. $^1H$ NMR ($CD_2Cl_2$, 400 MHz) δ: 12.02 (1H, s), 7.89-7.86 (1H, m), 7.52-7.47 (2H, m), 7.40-7.27 (7H, m), 6.90-6.86 (4H, m), 5.67-5.66 (1H, m), 4.14-4.09 (1H, m), 4.06-4.02 (1H, m), 4.00-3.85 (2H, m), 3.83 (6H, s), 3.74-3.68 (1H, m), 3.52-3.27 (3H, m), 3.21-3.17 (1H, m), 2.88-2.60 (5H, m), 1.27-1.22 (12H, m), 1.19-1.15 (6H, m). $^{13}C$ NMR ($CD_2Cl_2$) δ: 179.29, 178.97, 158.67, 147.82, 144.93, 136.17, 135.74, 130.04, 128.04, 127.79, 126.79, 121.16, 121.06, 118.49, 118.07, 113.06, 86.12, 81.61, 81.46, 77.15, 77.03, 76.77, 64.31, 64.24, 60.23, 59.51, 59.27, 50.39, 50.20, 48.20, 47.53, 47.19, 46.67, 46.64, 45.54, 45.48, 43.81, 43.69, 43.53, 43.42, 36.22, 35.97, 24.55, 24.47, 24.43, 24.35, 24.24, 24.17, 24.03, 20.79, 20.71, 20.62, 20.56, 20.48, 18.76, 18.63, 18.58. ESI-ESI-MS (m/z): 839.4019 $(M+H)^+$.

Solid Phase Synthesis: The procedure used to synthesize TMO and TMO-DNA chimeras is described in the synthesis scheme depicted in FIG. 4C: Prior to synthesis, the 5'-O-DMTr group on 2'-deoxythymidine as shown (A) or another nucleoside (2'-OMe-ribouridine, 2'-deoxynucleoside or morpholino nucleoside) linked to a controlled pore glass support was removed with 3% trichloroacetic acid in dichloromethane. The 5'-unprotected nucleoside (A) was then allowed to react (5 minutes) with compounds 19, 20, 21, or 22 in anhydrous acetonitrile containing a 0.12 molar solution of 4,5-dicyanoimidazole (DCI) as shown in FIG. 4C or 5-(ethylthio)-1H-tetazole to generate a dimer having a phosphoramidite-diester-internucleotide linkage (B). This intermediate was converted to (D') by treatment with 3-((N,N-dimethyl aminomethylidene)amino)-3H-1,2,4-dithiazole-5-thione (DDTT) for sulfurization and the support was next treated with a solution of acetic anhydride in order to cap any unreacted 5'-hydroxyl groups. For the preparation of thiophosphoramidate morpholino DNA chimeras (TMO/DNA), the synthesis cycle was similar except that 0.12M 5-(ethylthio)-1H-tetrazole was the activator with 5'-O-dimethoxytrityl-2'-deoxyribonucleoside-3'-phosphoramidite synthons (23, 24, 25, or 26) to obtain (C). This phosphite triester was then converted to (E) by oxidation with DDTT to generate phosphorothioate internucleotide linkages or with aqueous iodine to generate a phosphate linkage. The products of these condensations (E) were then capped with acetic anhydride. Following treatment with 3% trichloroacetic acid in dichloromethane, (F') or (G) were ready for repetitions of the appropriate cycle to generate the TMO or TMO-DNA chimeras. These TMO and TMO-DNA chimeras were characterized by LCMS.

Automated TMO Synthesis: Syntheses were carried out on an ABI 394 Synthesizer. All syntheses were performed at a 1.0 μmol scale using a 5'-DMTr-2'-OMe-ribouridine joined to a CPG solid support via a succinate linkage. For the synthesis of thiomorpholino oligonucleotides, the phosphordiamidites (19, 20, 21, or 22; 0.1 M) were dissolved in anhydrous $CH_3CN$. The standard 1.0 μmole synthesis cycle was used with an increase in coupling time to 300 s. Following oxidation and capping, detritylations were carried out using a 3% solution of trichloroacetic acid in dichloromethane. A stepwise description of the synthesis cycle is described in Table 6. All syntheses were carried out with DMT ON. Following synthesis, resins were transferred to a 1.5 mL screw cap vial and treated with 1.0 mL $NH_4OH$ (37%) for 18 h at 55° C.

TABLE 6

Chemical Steps used to Prepare Thiomorpholino Oligonucleotides.

| Reactions | Wash/reagents/solvents | Time (s) |
|---|---|---|
| Detritylation | 3% trichloroacetic acid in dichloromethane | Flow 90 s |
| Condensation | 0.1M phosphordiamidite 19, 20, 21, or 22 (in $CH_3CN$) + Activator (0.12M dicyanoimidazole in $CH_3CN$) or | Wait 300 s |
| | 0.1M phosphoramidite 23, 24, 25, or 26 in $CH_3CN$ + Activator (0.25M ethylthio tetrazole in $CH_3CN$) | Wait 180 s |
| Sulfurization | 3-((N,N-dimethylaminomethylidene)amino)-3H-1,2,4-dithiazole-5-thione in pyridine, acetonitrile; 3:2 | Flow 15 s, wait 90 s |
| Wash | Anhydrous $CH_3CN$ | Flow 10 s |
| Capping | Cap A (THF/Pyridine/$Ac_2O$) + Cap B (16% 1-methyl imidazole in THF) | Flow 10 s, wait 5 s |
| Wash | Anhydrous $CH_3CN$ | Flow 10 s |
| Wash | Anhydrous $CH_2Cl_2$ | Flow 25 s |

The RP-HPLC purification protocol: A linear gradient of 0 to 40% B over 301.0 min at a flow rate of 1.0 Room Temperature mL/min; buffer A: 50 mM TEAB, pH 8.5; buffer B: acetonitrile 40%, Room Temperature. Column specifications:)(Bridge Oligonucleotide BEH C18 Prep Column, 130 Å, 2.5 µm, 10 mm×50 mm. This purification step yields the product as a broad peak due to the presence of multiple chiral phosphorus centers.

LC-MS analyses were carried out on an Agilent 6530 series Q-TOF LC/MS spectrometer. A waters ACQUITY UPLC BEH C18, 1.7 µm, 2.1×100 nm column was used with a gradient of 0-100% of buffer B in 50 min with a flow rate of 0.2 mL/min (Buffer A was 1:380:10:10.4 mixture of triethylamine:water:methanol:hexafluoro-2-propanol and Buffer B was 1:370:20:10.4 mixture of triethylamine:methanol:water:hexafluoro-2-propanol).

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A method of preparing a phosphorodiamidite monomer having a phosphorodiamidite moiety attached to the 3'-nitrogen of a morpholino ring comprising:
   a. contacting a 5'-O-Dimethoxytrityl ribonucleoside with sodium periodate and ammonium biborate to produce a dihydroxyribose morpholino monomer, wherein the base is one of uracil, thymine, cytosine, adenine, hypoxanthine, and guanine, optionally protected at the nucleoside amino groups by a protecting group,
   b. reducing hydroxyl groups on the dihydroxyribose morpholino monomer with sodium cyanoborohydride to produce a morpholino monomer, and
   c. phosphitylating the morpholino monomer with 2-cyanoethyl-N,N,N',N'-tetraisopropylphosphorodiamidite and 4,5-dicyanoimidazole (DCI) in dichloromethane to produce a phosphorodiamidite monomer.

2. The method of claim 1, wherein steps a-c generate a synthon having a chemical structure according to Formula I:

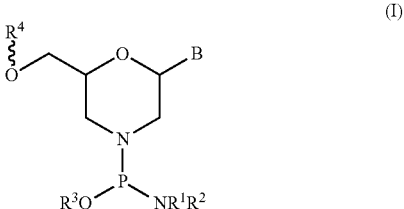

(I)

wherein:
   B is independently a nucleic acid base selected from the group consisting of adenine, guanine, uracil, thymine, cytosine, and hypoxanthine, or a nucleic acid base protected with a silyl protecting group or an acid-labile or base-labile protecting group;
   $R^1$ and $R^2$ are independently $C_{1-7}$ alkyl or aryl optionally substituted with one or more heteroatoms;
   $R^3$ is a protecting group that can be removed following synthesis of an oligonucleotide, such as cyanoethyl or methyl; and
   $R^4$ is a linker selected from a phosphate linkage, a phosphorothioate linkage, a phosphorodiamidate linkage or a boranophosphate linkage; wherein the linker is linked to dimethoxytrityl protecting group, a phosphorus derivative, a DNA or RNA nucleotide/oligonucleotide, trimethoxytrityl, dimethoxytrityl, monomethoxy-trityl, trityl, any silyl, or another morpholino of formula I.

3. The method of claim 2, wherein the nucleoside amino base protecting group is selected from the group consisting of:

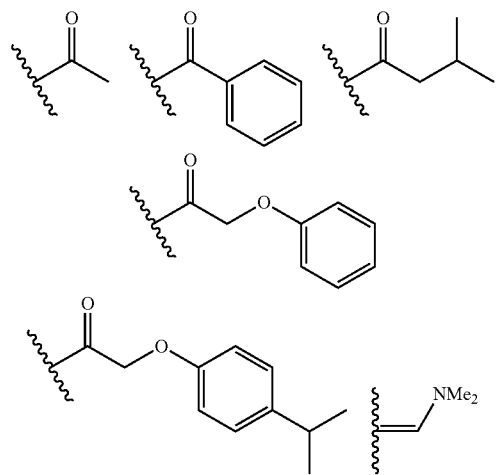

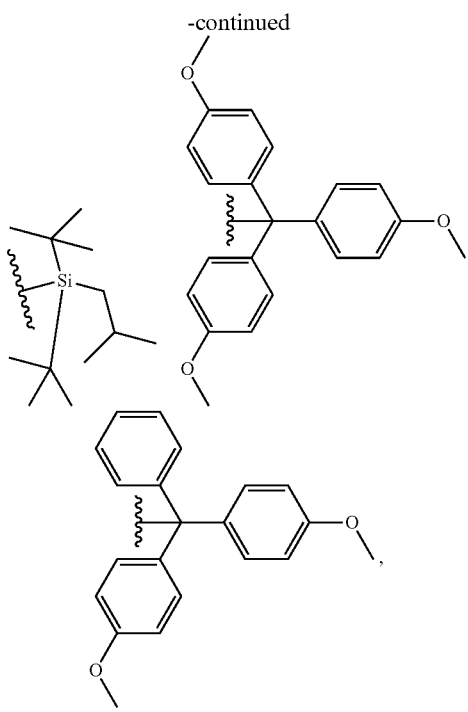

and a protecting group of claim 2.

4. A method of forming an oligonucleotide comprising at least one monomeric subunit generated by the method of claim 1, comprising:
   a. providing a 5'-unprotected-2'-deoxyribonucleoside, a 6'-unprotected morpholino nucleoside, or a ribonucleoside having a 2'-alkoxy or 2'-halogen linked to a polystyrene/CPG support;
   b. reacting the 5'-unprotected-2'-deoxyribonucleoside, a 6'-unprotected morpholino nucleoside, or a ribonucleoside having a 2'-alkoxy or 2'-halogenlinked to a polystyrene/CPG support with the phosphorodiamidite synthon of Formula I of claim 2 in anhydrous acetonitrile containing 4,5-dicyanoimidazole (DCI), tetrazole, S-ethyltetrazole, or other activator, to generate a dimer having a phosphoramidite diester internucleotide linkage;
   c. chemically activating the dimer comprising at least one of boronating, sulfurizing, or oxidizing the dimer phosphoramidite internucleotide linkage,
   d. capping the dimer,
   e. detritylating the dimer,
   f. repeating steps b to e to elongate the oligonucleotide using the phosphoramidite synthon of Forumla I of claim 2, a 2'-deoxynucleoside 3'-phosphoramidite, or a 2'-protected ribonucleoside 3'-phosphoramidite,
   g. converting the phosphoramidite synthon of Forumla I of claim 2, 2'-deoxynucleoside 3'-phosphoramidite, or 2'-protected ribonucleoside 3'-phosphoramidite internucleotide linkages to morpholino thinophosphoramidate or phosphoramidate, morpholinoboranophosphate, 2'-deoxynucleoside 3'-thiophosphate or phosphate, or 2'-protected ribonucleoside 2'-protected ribonucleoside 3'-thiophosphate or phosphate, wherein said step of converting comprises sulfurization with a sulfurizing reagent, oxidation with an oxidation reagent, or boronation with a boronating reagent,
   h. contacting morpholino borane phosphoroamidate monomers with iodine and an amine in tetrahydrofuran to convert morpholino borane phosphoroamidate to amino-phosphorodiamidate morpholinos (PMOs),
   i. contacting the oligomer with a solution comprising ammonium hydroxide and ethylene diamine to remove the oligomer from the polystyrene support and to remove base labile protecting groups or contacting the oligomer with a fluoride solution or acidic solution to remove either silyl or acid labile protecting groups followed by ammonium hydroxide and ethylene diamine toremove the oligomer from the support, and
   j. contacting the oligomer with a mild acid or other reagent to remove the 5'-protecting group R
   wherein steps a-i generate an oligomer comprising a monomer subunit having the chemical structure of Formula II:

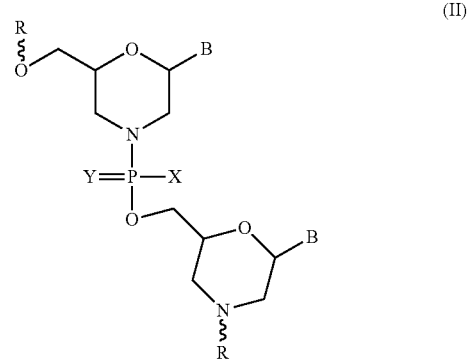

wherein:
   each B is independently a nucleic acid base (adenine, guanine, uracil, thymine, cytosine, hypoxanthine);
   X is oxygen or sulfur, methyl, ethyl, any $C_{3-7}$ alkyl, a 5-7 membered aliphatic or aromatic ring, carboxylate, acetate or formate derivatives, $NH_3$, an amine, or amine substituted with any linear or branched $C_{2-5}$ alkyl;
   Y is oxygen or sulfur; and
   each R is independently linked to a glass substrate, a polystyrene resin, dimethoxytrityl protecting group, a phosphorus derivative, a DNA or RNA nucleotide/oligonucleotide, trimethoxytrityl, dimethoxytrityl, monomethoxy trityl, trityl, any silyl, or another morpholino of formula I, wherein the linker is phosphorodiamidate linker with phosphate/phosphorothioate/bornaphosphate linkages, or a phosphoroamidate linker, a phosphate linkage, or a thiophosphoramidate linkage, or any other linkage with a morpholino ring with X.

5. The method of claim 4, wherein the nucleic acid base protecting group is selected from the group consisting of:

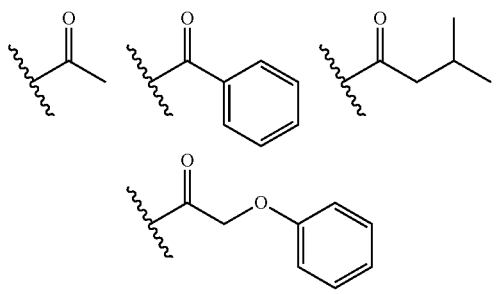

-continued

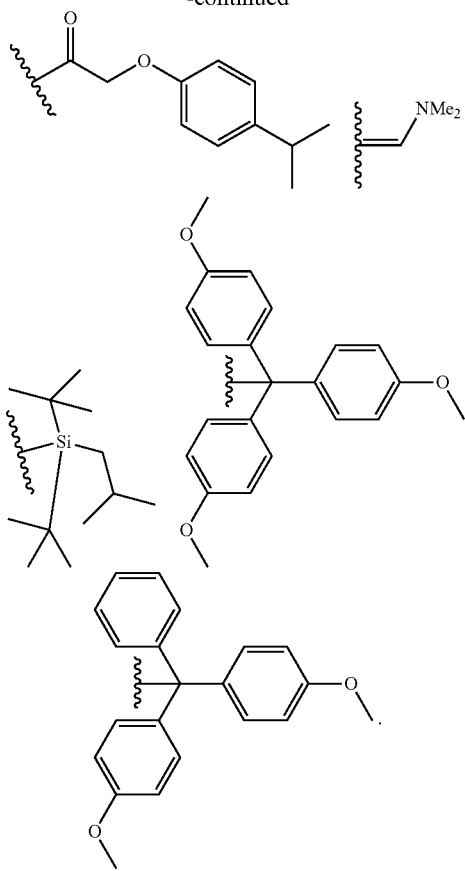

6. The method of claim 4, wherein the oligomer has between 2 and 40 monomeric subunits.

7. The method of claim 4, wherein the activating step c comprises boronating the dimer and further comprising the additional step of: removing cyanoethyl groups from the internucleotide linkages after the elongating step f and before the contacting step h.

8. The method of claim 4, wherein the activating step c comprises boronating the dimer and further comprising the additional step of: contacting the monomers with a solution of tetrabutyl ammonium fluoride (TBAF) in THF to remove BIBS protecting groups from the monomers, after the contacting step h and before step i.

9. The method of claim 4, wherein the repeating synthesis step f is conducted on a commercial DNA synthesizer.

10. The method of claim 4, wherein after sulfurizing to generate a thiomorpholino linkage the oligomer synthesized comprises at least one monomer subunit of claim 4.

11. An oligonucleotide produced by the method of claim 4, comprising thiomorpholino internucleotide linkages that form duplexes with complementary DNA or RNA.

12. An oligonucleotide produced by the method of claim 4, that activates RNAse H1 enzymatic activity.

13. An oligonucleotide produced by the method of claim 4, that inactivates RNA, DNA, or enzymatic activity.

14. An oligonucleotide produced by the method of claim 4, that is transfected into cells by gymnosis, electroporation, or using lipid reagents.

15. The method of any one of claim 4, wherein after sulfurizing to generate the thiomorpholino linkage the oligomer synthesized has a combination of thiophosphoramidate morpholino, 2'-deoxyribonucleotide, and ribonucleotide internucleotide linkages or oligomers having all thiophosphoramidate morpholino linkages.

* * * * *